Figure 1:
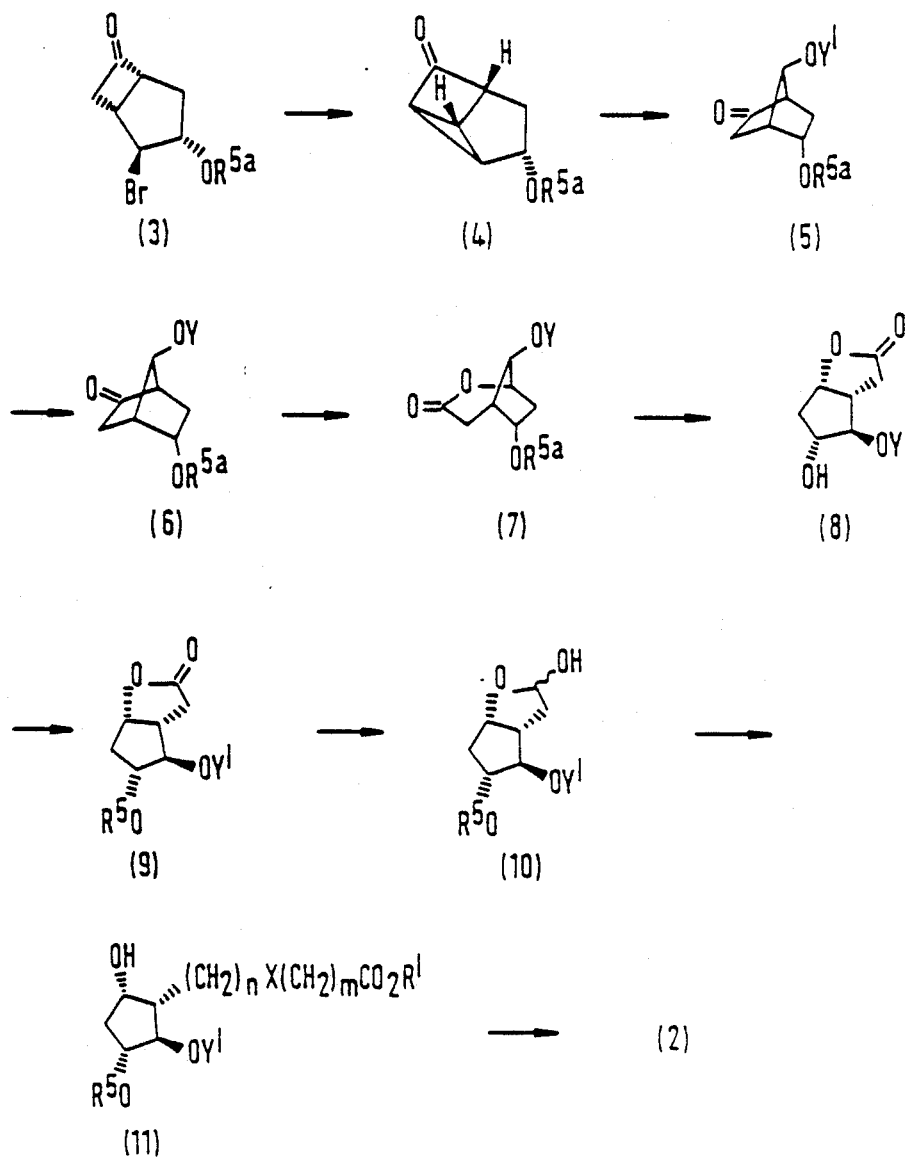

United States Patent [19]

Collington

[11] Patent Number: 4,837,363
[45] Date of Patent: Jun. 6, 1989

[54] CYCLOPENTYL ETHERS AND THEIR PREPARATION AND PHARMACEUTICAL FORMULATION

[75] Inventor: Eric W. Collington, Welwyn, England

[73] Assignee: Glaxo Group Limited, London, England

[21] Appl. No.: 726,332

[22] Filed: Apr. 23, 1985

[30] Foreign Application Priority Data

Apr. 24, 1984 [GB] United Kingdom ............... 8410396

[51] Int. Cl.$^4$ ............................................. C07C 177/00
[52] U.S. Cl. ........................................ 560/053; 560/9; 560/11; 514/530; 514/571; 562/463; 562/426; 562/429
[58] Field of Search ............... 560/53, 9, 11; 562/463, 562/426, 429; 514/530, 571

[56] References Cited

FOREIGN PATENT DOCUMENTS

EP63337 10/1982 European Pat. Off. .

OTHER PUBLICATIONS

Novak, L. et al. Acta Chim. Hung. 113(4) 355-365 1983.

Primary Examiner—Paul J. Killos
Attorney, Agent, or Firm—Bernard, Rothwell & Brown

[57] ABSTRACT

Compounds are described of formula (1)

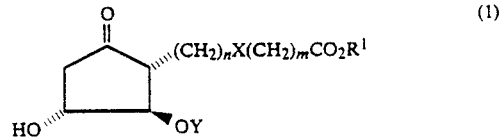

in which
n is 1 or 2;
m is 2–5 and X is —CH=CH— or —CH$_2$CH$_2$—, or m is 1–4 and X is —CH=C=CH—;
R$^1$ is —H, C$_{1-6}$ alkyl or C$_{7-10}$ phenalkyl,
Y substituted or unsubstituted 3-phenoxy-2-hydroxypropyl,
and their salts.

These compounds inhibit gastric acid secretion and provide gastrointestinal cytoprotection, and may be formulated for use in the treatment of ulcers.

10 Claims, 4 Drawing Sheets

CYCLOPENTYL ETHERS AND THEIR PREPARATION AND PHARMACEUTICAL FORMULATION

Prostaglandin $E_2$ is a naturally occurring substance which has many physiological actions. For example, it inhibits gastric acid secretion and provides gastrointestinal cytoprotection, lowers blood pressure, stimulates and relaxes smooth muscle, inhibits platelet aggregation and inhibits lipolysis.

Synthetic $PGE_2$ analogues offer the possibility of different potency, longer duration of activity and increased selectivity of action and are therefore of considerable interest.

Many different $PGE_2$ analogues have been suggested in the past for use in medicine but in only one instance have 13-oxa compounds been proposed in this respect. Thus, British patent specification No. 2082176A describes a group of compounds which includes 2-(heptyloxy)-3-hydroxy-5-oxo-cyclopentaneheptanoic acid and a 15- hydroxy derivative thereof. These compounds are stated to inhibit blood platelet aggregation and have bronchodilatory activity, and are proposed for use as antithrombotic or antiasthmatic agents.

We have now found a new group of cyclopentyl ethers having $PGE_2$-type acitivty. Compounds in this class have in particular shown high potency and extended duration of action as regards the inhibition of gastric acid secretion and gastrointestinal cytoprotection and are therefore of interest in the treatment of ulcers.

The invention thus provides compounds of the general formula (I)

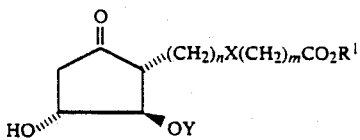

wherein n is 1 or 2;

m is 2–5 and X is cis or trans —CH=CH— or $CH_2$—$CH_2$—; or m is 1–4 ad X is —CH=C=CH—;

$R^1$ is a hydrogen atom, $C_{1-6}$ alkyl or $C_{7-10}$ phenalkyl; and Y is

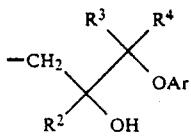

where $R^2$, $R^3$ and $R^4$ are each a hydrogen atom or methyl and at least one is a hydrogen atom, and Ar is a phenyl group (optionally substituted by one or two $C_{1-4}$ alkyl, $C_{1-4}$ alkoxy, $C_{1-4}$ alkylthio, $C_{1-4}$ alkylsulphinyl, $C_{1-4}$ alkylsulphonyl, halogen or trifluoromethyl groups);

and the physiologically acceptable salts and solvates thereof.

The structural formula herein are to be understood to include the enantiomers of each of the compounds concerned as well as mixtures of the enantiomers including racemates.

In general, the compounds of formula (I) in which the carbon atom carrying the group —$(CH_2)_n X(CH_2)_m CO_2 R^1$ and/or the carbon atom in the group Y carrying the —OH group are in the R-configuration (particularly the former) and mixtures containing such isomers are preferred.

The alkyl groups referred to above in the definition of the compounds of formula (I) may be straight or branched.

Compounds of formula (I) in which $R^1$ is a hydrogen atom can form salts with bases. Examples of such salts are alkali metal (e.g. sodium), alkaline earth metal (e.g. calcium) and amine (e.g. piperazine) salts.

In compounds where X is —CH=CH— or —$CH_2CH_2$—, m is preferably 3 when n is 1, and m is preferably 2 or 4 when n is 2. When X is —CH=C=CH—, m is preferably 2 when n is 1 and 1 or 3 when n is 2.

Examples of suitable $R^1$ groups are $C_{1-3}$ alkyl, benzyl and phenethyl. $R^1$ is preferably $C_{1-3}$ alkyl (e.g. a methyl or isopropyl) or a hydrogen atom, particularly methyl.

In the group Y, $R^3$ and $R^4$ are preferably hydrogen atoms. Compounds in which $R^2$ is H or —$CH_3$ and $R^3$ and $R^4$ are hydrogen atoms are also preferred.

When the Ar phenyl group is substituted, the substituent may for example be methyl, ethyl, propyl, butyl, methoxy, ethoxy, propoxy, butoxy, methylthio, methylsulphinyl, methylsulphonyl, fluoro, chloro, bromo or trifluoromethyl. Preferably only a single substituent is present, particularly at the para-position. In general, Ar is preferably phenyl or phenyl substituted by halogen, particularly fluoro or chloro.

The preferences indicated above apply both separately and in combination with one or more of the other stated preferences.

A preferred group of compounds of the invention thus has the formula (I) in which:

X is —CH=CH— or —$CH_2CH_2$— and n is 1 and m is 3 or n is 2 and m is 2 or 4 or X is —CH=C=CH and n is 1 and m is 2 or n is 2 and m is 1 or 3;

$R^1$ is a hydrogen atom or $C_{1-3}$ alkyl (particularly methyl);

$R^2$ is a hydrogen atom or methyl;

$R^3$ and $R^4$ are hydrogen atoms;

Ar is phenyl or phenyl substituted by fluoro or chloro; including the physiologically acceptable salts and solvates thereof.

Compounds of this type in which the carbon atom carrying the —$(CH_2)_n X(CH_2)_m CO_2 R^1$ group is in the R- configuration are particularly preferred.

Particularly important compounds of the invention are:

[1R-[1α(Z),2β,(R*),3α]]-(−)-Methyl  7-[3-hydroxy-2-(2-hydroxy-3-phenoxypropoxy)-5-oxocyclopentyl]-5-heptenoate

[1R-[1α(Z),2β,3α]]-(−)-Methyl  7-[3-hydroxy-2-(2-hydroxy-3-phenoxypropoxy)-5-oxocyclopentyl]-5-heptenoate

[1R-[1α(Z),2β,3α]]-(−)-Methyl  7-[2-[3-(4-fluorophenoxy)-2-hydroxypropoxy]-3-hydroxy-5-oxocyclopentyl]-5-heptenoate

[1R-[1α(Z),2β,3α]]-(−)-Methyl  7-[2-[3-(4-chlorophenoxy)-2-hydroxypropoxy]-3-hydroxy-5-oxocyclopentyl]-5-heptenoate

[1R-[1α(Z),2β,(R*),3α]]-7-[3-hydroxy-2-(2-hydroxy-3-phenoxypropoxy)-5-oxocyclopentyl]-5-heptenoic acid and its physiologically acceptable salts

[1R-[1α(Z),2β,3α]]-(−)-Methyl  7-[3-hydroxy-2-(2-hydroxy-3-phenoxypropoxy)-5-oxocyclopentyl]-4-heptenoate

[1R-[1α(Z),2β,3α]]-(−)-Methyl 7-[3-hydroxy-2-(2-hydroxy-2-methyl-3-phenoxypropoxy)-5-oxocyclopentyl]-5-heptenoate

[1R-[1α(E),2β(R*),3α]]-Methyl 7-[3-hydroxy-2-(2-hydroxy-3-phenoxypropoxy)-5-oxocyclopentyl]-5-heptenoate

[1R-[1α(Z),2β(R*),3α]]-(−)-1-Methylethyl 7-[3-hydroxy-2-(2-hydroxy-3-phenoxypropoxy)-5-oxocyclopentyl]-5-heptenoate, and

[1R-[1α,2β,3α]]-(−)-Methyl 7-[3-hydroxy-2-(2-hydroxy-3-phenoxypropoxy)-5-oxocyclopentyl]-4,5-heptadienenoate.

Compounds of formula (I) inhibit gastric acid secretion, as determined for example by their ability to inhibit histamine-induced secretory responses in the rat perfused stomach, following the method of Ghosh M. N. and Schild in Br. J. Pharmacol., 1958, 13, 54 as modified by Parsons M. E., Ph.D Thesis, University of London, 1969.

The compounds also provide gastrointestinal cytoprotection, as determined for example by their ability to inhibit ethanol-induced lesions in the conscious rat, following the method of Robert et al in Gastroenterology, 1979, 77, 433, modified by the use of 5 mg/kg/s.c. indomethacin prior to the administration of the test compound.

The compounds are thus of interest in the prevention and/or treatment of ulcers. They may also be used in the treatment of other conditions which arise from the hypersecretion if gastric acid. They may be formulated in conventional manner with one or more pharmaceutical carriers, for example for oral, buccal, parenteral or rectal administration.

The compounds may be formulated for oral administration as, for example, tablets, capsules, powders, solutions or syrups prepared by conventional means with acceptable excipients, optionally in the presence of a stabilising agent.

The compounds may be formulated for parenteral administration by bolus injections or continuous infusion. Formulations for injections may be presented in unit dosage form in ampoules, or in multi-dose containers, with an added preservative.

For buccal administration, the compounds may be formulated as tablets or lozenges in conventional manner; and for rectal administration compositions such as suppositories or retention enemas, for example containing conventional suppository bases such as cocoa butter or other glyceride, can be used.

The compounds are preferably administered orally, for example in amounts of 0.5 to $300 \times 10^6$ g/kg body weight, 1 to 4 times daily. For parenteral administration, the compounds may be administrated in amounts of 0.01 to $10^{-6}$ g/kg body weight, 1 to 4 times daily. The precise dose will of course depend on the age and condition of the patient.

Suitable methods for preparing the compounds of the invention are described below, the various groups and symbols being as defined above except where otherwise indicated.

(a) Compounds of formula (I) may be prepared by deprotection of a corresponding compound in which the ring hydroxy group and the hydroxy group in Y are protected.

The protected compounds are thus of formula (2)

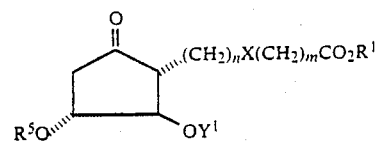

(2)

in which $R^5$ is a suitable hydroxyl protecting group (e.g. tetrahydropyran-2-yl, tri(hydrocarbyl)silyl or arylmethyl) and Y' is defined as a group

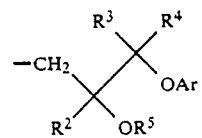

The two $R^5$ groups in the compounds of formula (2) are conveniently the same, but they may be different if desired.

Where $R^5$ is tri(hydrocarbyl)silyl the hydrocarbyl substituents may be the same or different e.g. $C_{1-6}$ alkyl, $C_{2-6}$ alkenyl, $C_{3-7}$ cycloalkyl, $C_{7-20}$ aralkyl and $C_{6-20}$ aryl groups. Such groups include methyl, ethyl, n-propyl, isopropyl, n-butyl, isobutyl, t-butyl, allyl, phenyl and benzyl. Preferred hydrocarbyl groups are $C_{1-4}$ alkyl, e.g. methyl and t-butyl. Trimethylsilyl and t-butyldimethylsilyl groups are particularly preferred.

When $R^5$ is an arylmethyl group it may contain up to 20 carbon atoms, e.g. benzyl, diphenylmethyl or triphenylmethyl.

The method used to deprotect the protected hydroxyl group depends on the nature of $R^5$ but in general acid hydrolysis or reduction may be used.

Deprotection may be carried out, when $R^5$ is a tetrahydropyran-2-yl group, with an acid (e.g. acetic acid, trifluoroacetic acid or a dilute mineral acid) in a suitable solvent (e.g. aqueous tetrahydrofuran) at an appropriate temperature (e.g. 45°).

A tri(hydrocarbyl)silyl group may for example be removed by acid hydrolysis, e.g. with dilute mineral acid or trifluoroacetic acid or by treatment with fluoride ions (e.g. from a quaternary ammonium fluoride such as tetra-n-butyl ammonium fluoride), or by treatment with aqueous hydrogen fluoride. Arylmethyl groups may be removed by reduction, e.g. by hydrogenolysis, e.g. with a noble metal catalyst such as platinum or palladium, or by treatment with a Lewis acid (e.g. boron trifluoride-etherate) in the presence of a thiol (e.g. ethanethiol) in a suitable solvent such as dichloromethane at e.g. room temperature.

Methods for preparing the compounds of formula (2) are described below in ((a)(i)–(vi)), from which it will be appreciated that the deprotection method (a) is usually applied in connection with the formation by oxidation of the ring oxo group. Thus, the compounds of formula (1) may generally be prepared by oxidising a corresponding compound having an α-OH group instead of the ring oxo group, the other hydroxy groups present (i.e. the ring hydroxy group and the hydroxy group in Y) being protected during the reaction, as described above.

(a)(i) Compounds of formula (2) in which X is cis —CH=CH— and n is 1 may be prepared by the reaction sequence shown in FIG. 1 of the drawings.

Norbornanones of formula (5) may be prepared by treating compounds of formula (3), where $R^{5a}$ is as defined above for $R^5$ or is another suitable hydroxyl protecting group (e.g. methoxymethyl or methoxyethoxymethyl), with Y'OH in the presence of a non-nucleophilic base (e.g. potassium t-butoxide, sodium hydride or sodium metal). The tricyclic intermediates of formula (4) are not usually isolated but can be formed by treating a ketone of formula (3) with a non-nucleophilic base. A compound of formula (5) can be prepared in a separate step, by treatment of a compound of formula (4) with Y'OH in the presence or absence of base.

Intermediates of formulae (3) and (4) may be prepared by the methods generally described in British patent specification Nos. 1568371 and 1568372. The alcohols Y'OH may be prepared from the known alcohols YOH by standard hydroxy protection procedures, for example those described in "Protective Groups in Organic Chemistry", Ed. J. F. W. McOmie (Plenum Press 1973).

Norbornanones of formula (6) may be prepared by selective removal of the $R^5$ protecting group present in the corresponding compounds of formula (5).

The lactones of formula (7) may be prepared by the Baeyer-Villiger oxidation of the corresponding norbornanone of formula (6) with a peracid. Deprotection of lactones of formula (7) provides the lactones of formula (8). The formation of compounds of formula (8) can occur spontaneously on removal of the group $R^{5a}$, but otherwise the deprotection step is followed by treatment with an acid (e.g. toluene-p-sulphonic acid).

The lactols of formula (10) may be prepared by first protecting the hydroxy groups of lactones of formula (8) (e.g. as the tetrahydropyran-2-yl ethers) to give lactones of formula (9). Subsequent reduction with for example di-isobutylaluminium hydride gives the lactols of formula (10).

Compounds of formula (11) may be prepared by reacting a lactol of formula (10) with an appropriate Wittig reagent $(R^6)_3P=CH(CH_2)_mCO_2R^1$ (where $R^6$ is $C_{1-6}$ alkyl or aryl, e.g. monocyclic aryl such as phenyl) or a salt thereof, e.g. the potassium salt. Suitable solvents include hydrocarbons (e.g. benzene and toluene), ethers (e.g. tetrahydrofuran) and dialkylsulphoxides (e.g. dimethylsulphoxide). The reaction may be carried out at any suitable temperature from $-70°$ C. to $50°$ C., preferably at room temperature. The reaction is particularly suitable for the preparation of compounds in which $R^1$ is hydrogen.

Compounds of formula (11) in which $R^1$ is hydrogen may also be prepared by hydrolysing a corresponding ester (e.g. a $C_{1-6}$ alkyl ester), e.g. using a base such as sodium hydroxide or potassium hydroxide in a suitable solvent (e.g. methanol) at room temperature to $50°$ C.

Compounds of formula (2) may be prepared by oxidation of a compound of formula (11) with for example pyridinium chlorochromate in the presence of a buffer (e.g. sodium acetate) in a suitable solvent (e.g. dichloromethane) at an appropriate temperature (e.g. room temperature). Alternatively, the oxidation may be carried out with dimethylsulphoxide, activated by N,N,'-dicyclohexylcarbodiimide, in the presence of pyridinium trifluoroacetate in a solvent such as dichloromethane at e.g. room temperature. Other conventional oxidative methods can also be used, for example Jones reagent.

If desired, a compound of formula (2) or formula (11) in which $R^1$ is a hydrogen atom may be converted to the corresponding compound in which $R^1$ is $C_{1-6}$ alkyl or $C_{7-10}$ phenalkyl by esterification using for example one of the processes described in Section (b) below. Also, the group X in the compound of formula (11) may be reduced to $-CH_2CH_2$ (e.g. by method (c) below) or isomerised to trans $-CH=CH-$ prior to the formation of the compound of formula (2). The isomerisation may for example be effected by treating the corresponding cis compound with toluene-p-sulphinic acid in dioxan (e.g. at reflux), or azobisisobutyronitrile and thiophenol, using for exmple a hydrocarbon solvent (e.g. benzene) at any suitable temperature up to reflux.

Figure 2:
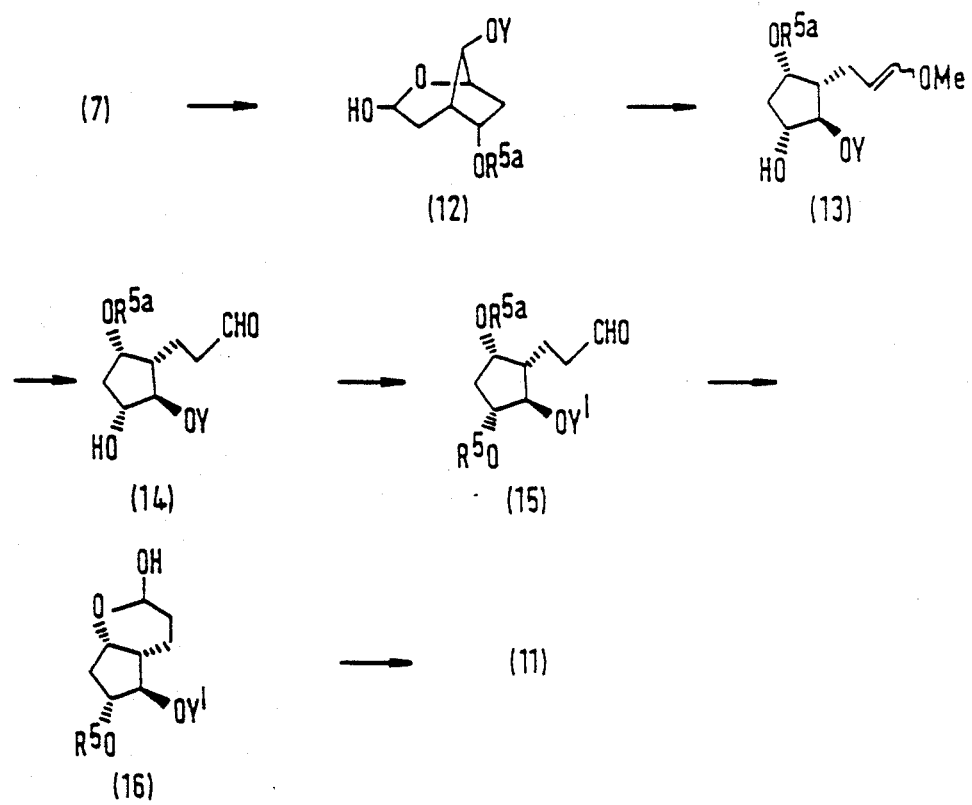

(a)(ii) Compounds of formula (2) in which X is cis $-CH=CH-$ and n is 2 may be prepared by the reaction sequence shown in FIG. 2.

A lactone of formula (7) is reduced, in the same manner as described above for reductions of lactones of formula (9), to give a lactol of formula (12) (or its aldehyde tautomer). Treatment with an appropriate Wittig reagent, (e.g. $(R^6)_3P=CHOR^7$, where $R^6$ is as dfined above and $R^7$ is $C_{1-4}$ alkyl), in a similar manner to that described in process a(i), gives the vinyl ether of formula (13) which is hydrolysed to the aldehyde (14) for example using a dilute acid such as hydrochloric acid in a suitable solvent (e.g. acetone). A protecting group $R^5$ (e.g. tetrahydropyran-2-yl group) is then introduced to give the aldehyde of formula (15) which on selective removal of the $R^{5a}$ protecting group e.g. the phenylmethyl group by hydrogenolysis by the method described above yields a lactol of formula (16).

Elaboration of a lactol of formula (16) to a compound of formula (2) is then performed as described in process (a)(i) for the conversion of compounds of formula (10) to those of formula (2).

Figure 3:
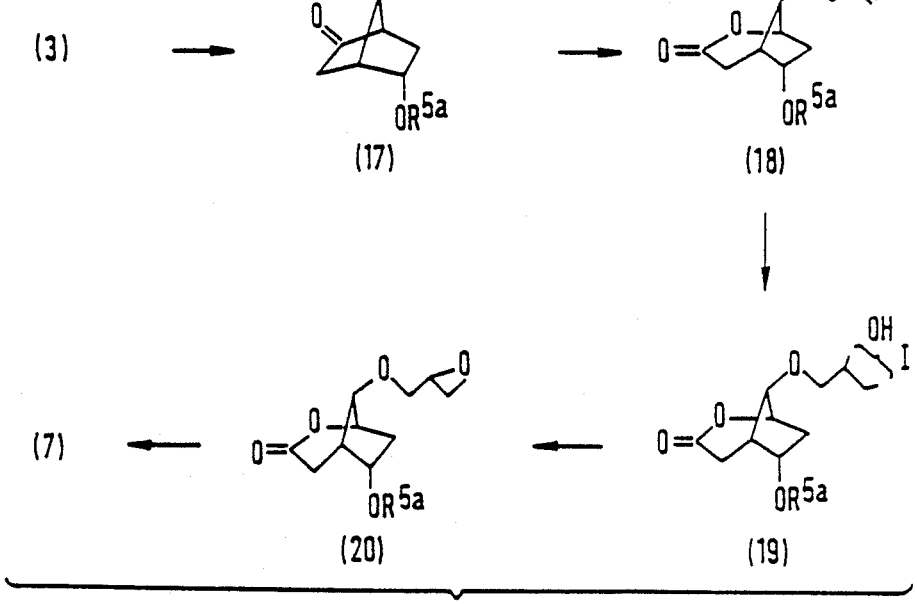

(a)(iii) Lactones of formula (7) may alternatively be prepared by the sequence shown in FIG. 3.

Firstly, a compound of formula (3) is reacted with allyl alcohol (e.g. in the presence of sodium) to give a compound of formula (17) which on Baeyer-Villiger oxidation gives a lactone of formula (18). Epoxidation with for example trifluoroperacetic acid in the presence of a weak base e.g. potassium carbonate or by a two-step procedure involving conversion into an iodohydrin mixture of formula (19) with silver I oxide and iodine in a suitable solvent (e.g. aqueous dioxan), followed by treatment with base (e.g. sodium hydroxide) gives an epoxide of formula (20). Treatment of an epoxide of formula (20) with a phenol, ArOH, in the presence of a base (e.g. potassium carbonate or potassium fluoride on a support for example elumina) gives the lactones of formula (7).

Figure 4:
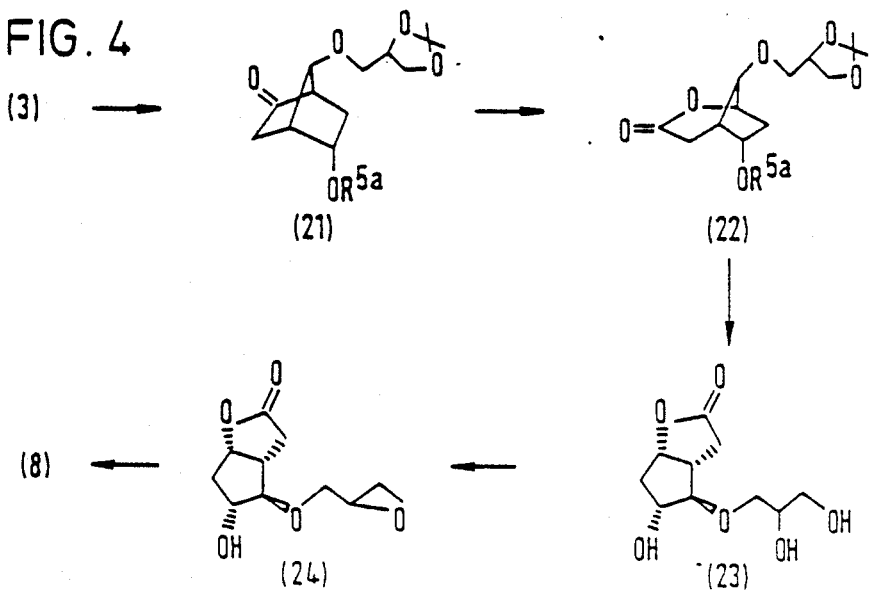

(a)(iv) Lactones of formula (8) may alternatively be prepared by the reaction sequence shown in FIG. 4.

A lactone of formula (22) may be prepared via a norbornanone of formula (21) using the general procedures described above. Deprotection and rearrangement gives a triol of formula (23) which obn reaction with diethyl azodicarboxylate in the presence of a phosphine, $(R^6)_3P$ (where $R^6$ is as defined above) at an appropriate temperature e.g. $70°$ C. provides an epoxide of formula (24). Reaction with a phenol, ArOH, in a similar manner to that described above for an epoxide of formula (20), gives the lactones of formula (8).

(a) (v) A lactone of formula (7) in which $R^2$ is a methyl group may be prepared by first oxidising a lactone of formula (7) in which $R^2$ is hydrogen (with for example Jones reagent) to give a ketone of formula (25). Subsequent reaction with a Grignard reagent (e.g. $CH_3MgCl$) in a suitable solvent (e.g. tetrahydrofuran) gives the lactone of formula (7).

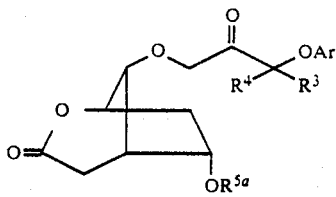

Figure 5:
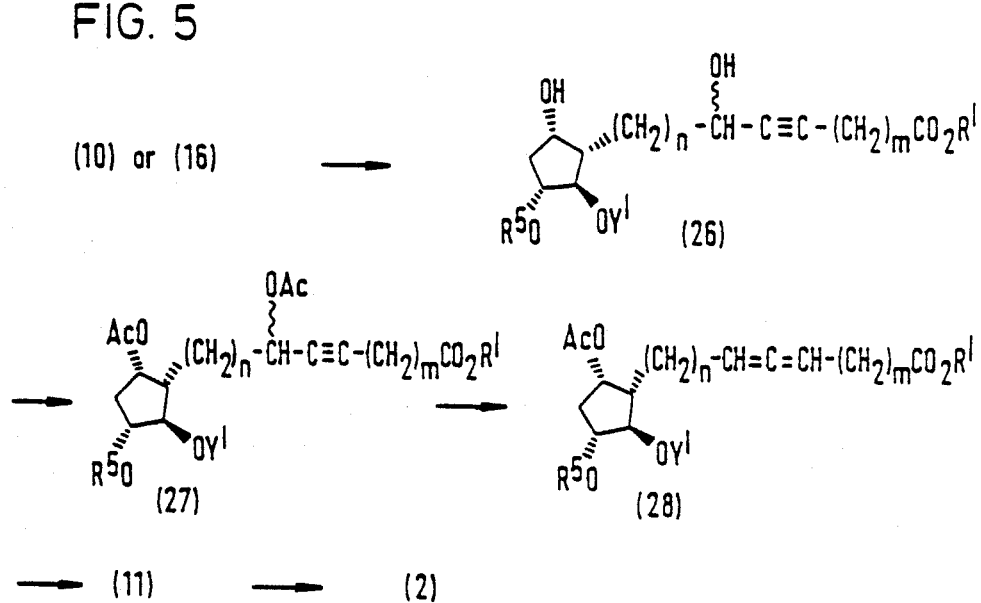

(a) (vi) Compounds of formula (2) in which X is —CH=C=CH— may be prepared by the reaction sequence shown in FIG. 5.

For example, a lactol of formula (10) or (16) in a suitable solvent (e.g. ether) is added to an excess of the dilithium salt of HC≡C(CH$_2$)$_m$COOH, at an appropriate temperature (e.g. 0°-25° C.). After esterification of the crude product with diazoalkane (e.g. diazomethane), a diol is given of formula (26). The lithium reagent may be prepared by the addition of the acid in a suitable solvent (e.g. ether or tetrahydrofuran) to the lithium salt of an amine (e.g. lithium diisopropylamide, prepared by the addition of an alkyl lithium (e.g. n-butyl lithium) to diisopropylamine in a suitable solvent (e.g. an ether-hexamethylphosphoramide mixture) at an appropriate temperature e.g. −78°-0° C.).

Acetylation of the diol of formula (26) (e.g. with acetic anhydride in the presence of 4-dimethylaminopyridine in a suitable solvent (e.g. a dichloromethane-triethylamine mixture) at an appropriate temperature (e.g. room temperature)) provides an acetylenic diacetate of formula (27). Subsequent reaction with an excess of lithium dimethylcopper (prepared as described, for example, by P. Rona et al., in J. Amer. Chem. Soc., 1969, 91, 3289) in a suitable solvent (e.g. ether) at an appropriate temperature (e.g. −78° C.) gives an allene of formula (28). Acetate hydrolysis with a base (e.g. potassium carbonate) in a suitable solvent (e.g. methanol) gives a compound of formula (11) where X s —CH=C=CH—, which may be converted into a compound of formula (2) by the method described above.

(b) Compounds of formula (1) in which R$^1$ is C$_{1-6}$ alkyl or C$_{7-10}$ phenalkyl may be prepared by esterifying the corresponding compound in which R$^1$ is a hydrogen atom.

Thus for example, compounds of formula (1) in which R$^1$ is a C$_{1-6}$ alkyl group may be prepared by esterification of the corresponding carboxylic acid with a diazoalkane e.g. diazomethane, in a suitable solvent (e.g. dichloromethane or ether) at room temperature.

Compounds of formula (1) in which R$^1$ is C$_{1-6}$ alkyl or C$_{7-10}$ phenalkyl may be prepared by conversion of the corresponding carboxylic acid into an activated derivative (e.g. a corresponding mixed anhydride) formed for example by reaction with an alkyl chloroformate (e.g. isobutyl chloroformate) in the presence of a suitable base (e.g. triethylamine or pyridine). The activated derivative can then be reacted with an appropriate alcohol, R$^1$OH, for example using a solvent such as acetone and a temperature of −10° C. to room temperature.

(c) Compounds of formula (1) in which X is a —CH$_2$—CH$_2$— group may be prepared by reduction of the corresponding compound in which X is a cis or trans —CH=CH— group or an acetylene group. Suitable methods of reduction include hydrogen in a presence of a catalyst, e.g. palladium, on a support (e.g. carbon).

Suitable solvents include ethyl acetate, ethanol and methanol.

(d) Compounds of formula (1) in which X is a —CH=CH-group may be prepared by selective reduction of a corresponding compound in which X is an acetylene group. Suitable methods of reduction include hydrogen in the presence of a catalyst, e.g. palladium on a support (e.g. CaCO$_3$ or BaSO$_4$) and poisoned for example by lead or quinoline. Suitable solvents include ethyl acetate and methanol. This reaction is particularly suitable for the preparation of compounds in which X is cis —CH=CH—.

The acetylenes required as starting materials may be prepared by first brominating (e.g. with bromine in CH$_2$Cl$_2$) a compound of formula (11) (in which the hydroxyl group is protected, X is —CH=CH— and R$^1$ is C$_{1-6}$ alkyl e.g. methyl) to give the corresponding compound in which X is —CHBr.CHBr. The latter dibromo compound is then dehydrobrominated to form the acetylene group, for example in two stages, using two potassium t-butoxide first at 0° C. and then at room temperature. Deprotection of the resulting compound affords a compound of formula (11) in which X is an acetylene group, which may then be converted into the required acetylene starting material by the methods described above for the conversion of compounds of formula (11) to compounds of formula (1). The R$^1$ group may if desired be modified before use in process (d).

(e) Compounds of formula (1) in which R$^1$ is a hydrogen atom may be prepared by hydrolysis of a corresponding ester. The ester is desirably a labile ester, for example a compound of formula (1) in which R$^1$ is tetrahydropyran-2-yl or tri(hydrocarbyl)silyl. Hydrolysis may be effected with an acid (e.g. acetic acid or trifluoroacetic acid) in a suitable solvent (e.g. aqueous tetrahydrofuran or dichloromethane) at an appropriate temperature.

(f) Where salts of compounds of formula (1) are desired such salts may be formed by conventional methods e.g. by treating an acid of formula (1) with a base (e.g. an amine such as piperazine) in a solvent such as ether.

When a specific enantiomer of formula (1) is required, starting materials having the desired stereochemical configuration should be used in the above processes. The bicyclic intermediates of formula (3) may be prepared for example from an enantiomeric bicycloheptenone as described in European Patent Specification No. 74856.

PHARMACEUTICAL EXAMPLES

In the examples given below the term "active ingredient" is used to denote a compound of the invention, such as the compounds described in the preceding examples, for example, the compound of Example 1.

1. Tablets

These may be prepared by direct compression.

|  | mg/tablet |
|---|---|
| Active ingredient | 0.015 to 0.2 |
| Magnesium stearate. BP | 1.5 |
| Microcrystalline cellulose, USP to compression weight | 150.0 |

The active ingredient is blended with about 10% of the microcrystalline cellulose then blended with the remaining microcrystalline cellulose and magnesium stearate. The blend is then compressed using 6 mm diameter punches into tablets on a suitable machine.

2. Capsules

|  | mg/capsules |
| --- | --- |
| Active ingredient | 0.015 to 0.2 |
| Magnesium stearate | 1.0 |
| *Starch 1500 to fill weight | 100.0 |

*A form of directly compressible starch

The active ingredient is preblended with some of the Starch 1500 then this preblend is mixed with the remaining Starch 1500 and magnesium stearate. The mix is then filled into size No. 2 hard gelatin capsule shells using suitable machinery. Other doses may be prepared by altering the amount of active ingredient in the blend and/or altering the fill weight and capsule size appropriately.

3. Sterile Solution

|  | μg/ml |
| --- | --- |
| Active ingredient | 0.1 to 1.0 |
| Ethanol BP to | 100.0 ml |

The sterile solution is added to normal saline or 5% dextrose and the mixture is administered intravenously.

The solution is prepared, clarified then sterilised by filtration and filled into sterile ampoules under aseptic conditions. The solution may be packed under an inert atmosphere of nitrogen or other suitable gas.

Temperatures are in 0° C.

The following abbreviations are used:

'Dried' refers to drying with anhydrous MgSO$_4$. T.l.c.—Thin Layer Chromatography on silica. Chromatography was carried out on silica gel.

ER—ether; EA—ethyl acetate; PE—petroleum ether (b.p. 60°-80° unless otherwise stated); DIBAL—diisobutylaluminum hydride; THF—tetrahydrofuran; CH$_2$Cl$_2$—dichloromethane; CHCl$_3$—chloroform; CHBr$_3$—bromoform; DMF—dimethylformamide; DMSO—dimethylsulphoxide; N.T.P.—normal temperature and pressure.

Intermediate 1

(2R)-3-Phenoxy-1,2-propanediol

Prepared as described in U.S. Pat. No. 4,322,557.

Intermediate 2

(2S)-(−)-1-[[(1,1-Dimethylethyl)diphenylsilyl]oxy]-3-phenoxy-2-propanol

A stirred soluton of Intermediate 1 (0.47 g) and imidazole (0.43 g) in DMF (20 ml), at 0°-5°, was treated with t-butylchlorodiphenylsilane (0.86 g) in DMF (10 ml) over 30 min. After 3 h the mixture was poured onto water (80 ml) and extracted with EA (3×50 ml). The combined extracts were washed with brine (2×30 ml), dried and evaporated to yield an oily residue. Purification by chromatography using 1:2 EA-PE as eluent gave the title compound as an oil (1.0 g).

I.r. (CHBr$_3$) $[\alpha]_D^{20}$ −4.8° (CH$_3$OH)

Intermediate 3

(2S)-(−)-(1,1-Dimethylethyl)[3-phenoxy-2-[(tetrahydro-2H-pyran-2-yl)oxy]propoxy]diphenylsilane A solution of Intermediate 2 (0.59 g), pyridinium toluene p-sulphonate (40 mg) and dihydropyran (0.17 ml) in CH$_2$Cl$_2$ (30 ml) was stirred at room temperature for 24 h. The mixture was washed successively with 8% NaHCO$_3$ (20 ml) and brine (2×20 ml) and then dried. Removal of the solvent gave a residue which was purified by chromatography using 2:9 ER-PE as eluent to give the title compound as an oil (0.3 g).

T.l.c. CH$_2$Cl$_2$ Rf 0.5 $[\alpha]_D^{19.4}$ −7.5° (CH$_2$OH)

Intermediate 4

(2S)-(−)-3-Phenoxy-2-[(tetrahydro-2H-pyran-2-yl)oxy]-1-propanol

Tetrabutylammonium fluoride (1M, 2.7 ml) was added to a stirred solution of Intermediate 3 (0.9 g) in THF (15 ml). After 1 h the solvent was removed in vacuo and the residue purified by chromatography using 3:2 EA-PE as eluent to give the title compound as solid (0.34 g), m.p. 39°-41°.

Intermediate 5

(1S)-(−)-Bicyclo[3.2.0]hept-2-en-6-one

Prepared as described in European Patent Specification No. 74856.

Intermediate 6

[1R-(1α,2α,3β,5α)]-(+)-2-Bromo-3-(phenylmethoxy)bicyclo[3.2.0]heptan-6-one

A mixture of Intermediate 5 (10 g) and benzylalcohol (54 g) at −5° was treated with N-bromosuccinimide (1.65 g) portionwise over 2 h. The mixture was stirred at −5° for 16 h, diluted with CH$_2$Cl$_2$ (100 ml) and washed with water (100 ml). The aqueous layer was extracted with CH$_2$Cl$_2$ (100 ml) and the combined organic extracts were washed successively with 5% sodium metabisulphite solution (50 ml) and water (50 ml). The organic extract was diluted with PE (330 ml), treated with powdered calcium chloride (60 g) and stirred at room temperature for 72 h. Filtration and evaporation gave a residue (28 g) which was crystallised from ethanol (32 ml) at −15° to give the title compound as a solid (13.6 g), m.p. 61°-61.5°. $[\alpha]_D^{22.5}$ +22.6° (CHCl$_3$)

Intermediate 7

(a)

[1R-[1R*,5S*,7(S*)]]-(+)-7-[[3-Phenoxy-2-(tetrahydro-2H-pyran-2-yl)oxy]propoxy]-5-(phenylmethoxy)bicyclo[2.2.1]heptan-2-one Sodium metal (1.3 g), in small pieces, was added to a solution of Intermediate 4 in THF (200 ml) and the mixture heated at reflux for 20 h. Unreacted sodium was removed by filtration and the filtrate treated with a solution of Intermediate 6 (7.08 g) in THF (40 ml). After 6 h stirring at room temperature a saturated solution of ammonium chloride (150 ml) was added and then the organic solvent removed in vacuo. The aqueous residue was extracted with ether (3×150 ml), the dried extracts were evaporated and the residue purified by chromatography using 3:7 EA-PE as eluent to give the title compound as an oil (7.7 g). I.r. (CHBr$_3$) 1740 cm$^{-1}$ $[\alpha]_D^{21.6}$ +26.1° (CH$_3$OH)

The following compounds were prepared in a similar manner:

(b) [1R-(Endo,Anti)]-(+)-7-[(2,2-Dimethyl-1,3-dioxolan-4-yl)methoxy]-5-(phenylmethoxy)bicyclo[2.2.1]heptan-2-one, from Intermediate 6.

I.r. (CHBr$_3$) 1742 cm$^{-1}$ [α]$_D^{24.1}$+29.6° (CH$_3$OH)

(c) [1R-(Endo,Anti)]-(+)-5-(Phenylmethoxy)-7-(2-propenyloxy)bicyclo[2.2.1]heptan-2-one, from Intermediate 6. I.r. (CHBr$_3$) 1740 cm$^{-1}$ [α]$_D^{21.4}$+41.2° (CH$_3$OH)

Intermediate 8

[1R-[1R*,4S*,5S*,7R*,7(R*)]]-(+)-7-(2-Hydroxy-3-phenoxypropoxy)-5-(phenylmethoxy)bicyclo[2.2.1]hepten-2-one A solution of Intermediate 7a (13.8 g) in methanol (150 ml) containing methanolic HCl (2.5 ml) was stirred for 2 h at room temperature. Water (150 ml) was added followed 1 h later by 8% NaHCO$_3$ solution (5 ml). The methanol was removed in vacuo and the aqueous residue extracted with ether (4×100 ml). The combined extracts were dried and evaporated to give the title compound as an oil (10.2 g).

I.r. (CHBr$_3$) 3580, 1745 cm$^{-1}$. [α]$_D^{22.8}$+23.7° (CH$_3$OH)

Intermediate 9

(a) [1R-[1R*,5S*,6S*,8R*,8(R*)]]-(−)-8-(2-Hydroxy-3-phenoxypropoxy)-6-phenylmethoxy-2-oxabicyclo[3.2.1]octan-3-one Peracetic acid (6.1M, 10.5 ml) was added dropwise during 10 min to a cold (0°), stirred mixture of Intermediate 8 (10.2 g) and sodium acetate (5.25 g) in CH$_2$Cl$_2$ (150 ml). After 24 h at room temperature the mixture was poured onto a 20% sodium sulphite solution (250 ml) and stirred for 1 h at 0°. The aqueous phase was extracted with CH$_2$Cl$_2$ (2×75 ml) and the combined extracts were dried and evaporated to give the title compound as an oil (9.35 g). I.r. (CHBr$_3$) 3570, 1725 cm$^{-1}$ (b) [1R-(Endo,Anti)]-(−)-8-(2-Hydroxy-3-phenoxypropoxy)-6-(phenylmethoxy)-2-oxabicyclo[3.2.1]octen-3-one A stirred mixture of Intermediate 24 (1.59 g), phenol (1.37 g) and potassium carbonate (2.3 g) in acetonitrile (7 ml) was heated at reflux for 4 h. Filtration and evaporation gave a residue which was purified by chromatography using ER as eluent to give the title compound as an oil (1.49 g). I.r. (CHBr$_3$) 3570, 1730 cm$^{-1}$. [α]$_D^{20}$−21.0° (CHCl$_3$)

The following compounds were prepared from Intermediate 24 in a similar manner:

(c) [1R-(Endo,Anti)]-(−)-8-[3-(4-Fluorophenoxy)-2-hydroxypropoxy]-6-(phenylmethoxy)-2-oxabicyclo[3.2.1]octan-3-one I.r. (CHBr$_3$) 3580, 1735 cm$^{-1}$. [α]$_D^{18.7}$−27.7° (CH$_3$OH)

(d) [1R-(Endo,Anti)]-(−)-8-[3-(4-Chlorophenoxy)-2-hydroxypropoxy]-6-(phenylmethoxy)-2-oxabicyclo[3.2.1]-octan-3-one I.r. (CHBr$_3$) 3580, 1740 cm$^{-1}$. [α]$_D^{20}$−26.2° (CH$_3$OH)

(e) [1R-(Endo,Anti)]-(−)-8-[3-(3-Chlorophenoxy)-2-hydroxypropoxy]-6-(phenylmethoxy)-2-oxabicyclo[3.2.1]octan-3-one I.r. (CHBr$_3$) 3580, 1735 cm$^{-1}$ [α]$_D^{18.5}$−25.9° (CH$_3$OH)

(f) [1R-(Endo,Anti)]-(−)-8-[3-(2-Chlorophenoxy)-2-hydroxypropoxy]-6-(phenylmethoxy)-2-oxabicyclo[3.2.1]octan-3-one I.r. (CHBr$_3$) 3580, 1738 cm$^{-1}$ [α]$_D^{19.3}$−29.3° (CH$_3$OH)

Intermediate 10

(a) [3aR-[3aα,4α(2R*),5β,6aα]]-(+)-Hexahydro-5-hydroxy-4-(2-hydroxy-3-phenoxypropoxy)-2H-cyclopenta[b]furan-2-one A solution of Intermediate 9a (9.35 g) in ethanol (150 ml) was hydrogenated over pre-reduced 10% palladium oxide on charcoal (2 g) at N.T.P. for 2 h. The catalyst and solvent were removed to give a residue whch was stirred in 2N NaOH (60 ml) for 2 h. The solution was extracted with ether (3×30 ml, discarded) and the aqueous phase acidified with 5N HCl and then stirred for 2 h. The solution was extracted with EA (4×50 ml) and the organic extracts were washed successively with 8% NaHCO$_3$ (4×50 ml) and brine (2×50 ml). Drying and evaporation gave an oil (2.01 g) a portion of which was triturated with CH$_2$Cl$_2$ and then crystallised from PE-methyl acetate to give the title compound as a powder m.p. 100°. [α]$_D^{24.3}$+16.1° (CH$_3$OH)

(b) [3aR-(3aα,4α,5β,6aα)]-(+)-Hexahydro-5-hydroxy-4-(2-hydroxy-3-phenoxypropoxy)-2H-cyclopenta[b]furan-2-one A solution of Intermediate 9b (1.0 g) in ethanol (30 ml) was hydrogenated over pre-reduced 10% palladium oxide on charcoal (0.1 g) at N.T.P. for 3 h. The catalyst and solvent were removed to give a residue (0.7 g) which was dissolved in CH$_2$Cl$_2$ (20 ml) was treated with toluene-p-sulphonic acid (0.025 g). After 24 h at ambient temperature the mixture was washed with 8% NaHCO$_3$ (20 ml) and brine (20 ml). The dried extracts were evaporated and the residue purified by chromatography using 20:1 CH$_2$Cl$_2$-methanol as eluent to give the title compound as a colourless oil (0.58 g).

I.r. (CHBr$_3$) 3590, 1770 cm$^{-1}$ [α]$_D^{19.2}$+9.5° (CH$_3$OH)

The following compound was prepared in a similar manner from Intermediate 9c:

(c) [3aR-(3aα,4α,5β,6aα)]-(+)-4-[3-(4-Fluorophenoxy)-2-hydroxypropoxy]-hexahydro-5-hydroxy-2H-cyclopenta[b]furan-2-one I.r. CHBr$_3$) 3590, 1768 cm$^{-1}$. [α]$_D^{19.7}$+9.0° (CH$_3$OH)

(d)

[3aR-(3aα,4α,6aα)]-(+)-4-[3-(4-Chlorophenoxy)-2-hydroxypropoxy]hexahydro-5-hydroxy-2H-cyclopenta[b]furan-2-one Boron trifluoride etherate (1.2 ml) was added to a mixture of Intermediate 9d (0.53 g) and ethanethiol (3 ml) in $CH_2Cl_2$ (5 ml). After 36 h at room temperature, water (10 ml) was added and the mixture was extracted with EA (3×15 ml). The combined extracts were washed with brine, dried and then evaporated. The residue was purified by chromatography using EA as eluent to give the title compound as a pale orange solid (0.42 g). I.r. (CHBr$_3$) 3590, 1768 cm$^{-1}$. $[\alpha]_D^{22.4}+6.1°$ (CH$_3$OH)

The following compounds were prepared in a similar manner:

(e)

[3aR-(3aα,4α,5β,6aα)]-(+)-4-[3-(3-Chlorophenoxy)-2-hydroxypropoxy[hexahydro-5-hydroxy-2H-cyclopenta[b]furan-2-one, from Intermediate 9e. I.r. (Nujol) 3500, 1725 cm$^{-1}$. $[\alpha]_D^{19.4}+7.8°$ (CH$_3$OH)

(f)

[3aR-(3aα,4α,5β,6aα)]-(+)-4-[3-(2-Chlorophenoxy)-2-hydroxypropoxy]hexahydro-5-hydroxy-2H-cyclopenta[b]furan-2-one, from Intermediate 9f. I.r. (CHBr$_3$) 3580, 1760 cm$^{-1}$. $[\alpha]_D^{22.1}+4.0°$ (CH$_3$OH)

(g)

[3aR-(3aα,4α,5β,6aα)]-(-)-Hexahydro-5-hydroxy-4-[2-hydroxy-3-(4-methoxyphenoxy)propoxy]-2H-cyclopenta[b]furan-2-one A stirred mixture of Intermediate 17 (0.3 g), K$_2$CO$_3$ (0.45 g) and 4-methoxyphenol (0.3 g) in acetonitrile (15 ml) was heated at reflux for 2 d. The mixture was treated with 2N HCl (10 ml), saturated with sodium chloride and then extracted with EA (4×50 ml). The dried extracts were evaporated and the residue purified by chromatography using 20:1 CH$_2$Cl$_2$-methanol as eluent to give the title compound as a gum (0.39 g). I.r. (CHBr$_3$) 3580, 1760 cm$^{-1}$ $[\alpha]_D^{19.3}+8°$ (CH$_3$OH)

The following compounds were prepared in a similar manner:

(h)

[3aR-(3aα,4α,5β,6aα)]-(+)-Hexahydro-5-hydroxy-4-[2-hydroxy-3-(3-methylphenoxy)propoxy]-2H-cyclopenta[b]furan-2-one, from Intermediate 17. I.r. (CHBr$_3$) 3580, 1765 cm$^{-1}$ $[\alpha]_D^{20}+6.8°$ CH$_3$OH)

(i)

[3aR-(3aα,4α,5β,6aα)]-(+)-Hexahydro-5-hydroxy-4-[2-hydroxy-3-[4-(methylthio)phenoxy]propoxy]-2H-cyclopenta[b]furan-2-one, from Intermediate 17.

I.r. (CHBr$_3$) 3580, 1760 cm$^{-1}$. $[\alpha]_D^{21.0}+9.4°$ (CH$_3$OH)

(j)

(3aα,4α,5β,6aα)-(+)-hexahydro-5-hydroxy-4-[2-hydroxy-3-[3-(trifluoromethyl)phenoxy]propoxy]-2H-cyclopenta[b]furan-2-one Peracetic acid (6.1M, 10.6 ml) was added dropwise to a cooled (0°), stirred, mixture of Intermediate 22 (5 g) and sodium acetate (4.6 g) in glacial acetic acid (25 ml) and water (10 ml). After 18 h at room temperature the excess peracetic acid was decomposed with a saturated sodium sulphite solution and the acetic acid was then removed in vacuo. The residue was diluted with water (50 ml), neutralised with 8% NaHCO$_3$ and extracted with EA (3×80 ml). The combined organic phases were washed with brine, dried and evaporated to yield a viscous oil (4.5 g). The crude product in ethanol (50 ml) was hydrogenated over pre-reduced 10% palladium oxide on charcoal (0.7 g) for 24 h. The catalyst and solvent were removed to yield a residual oil (3.43 g) which was dissolved in methanol (20 ml) and 5N NaOH (10 ml) and then heated at reflux for 15 min. The cooled, aqueous mixture was acidified with concentrated HCl and after 40 min at room temperature was extracted with CHCl$_3$ (2×50 ml). The combined organic phases were washed with 8% NaHCO$_3$ (2×30 ml), dried and evaporated to yield the title compound as a viscous oil (1.22 g).

I.r. (Neat) 3420, 1725 cm$^{-1}$

The following compound was prepared in a similar manner to Intermediate 10b.

(k)

[3aR-(3aα,4α,5β,6aα)]-(+)-Hexahydro-5-hydroxy-4-(2-hydroxy-2-methyl-3-phenoxypropoxy-2H-cyclopenta[b]furan-2-one, from Intermediate 27. I.r. (CHBr$_3$) 3580, 3500-3250, 1760 cm$^{-1}$ $[\alpha]_D^{17.8}+2.7°$ (CH$_3$OH)

Intermediate 11

(a)

[3aR-[3aα,4α(2R*),5β,6aα]]-(3O)-Hexahydro-4-[3-phenoxy-2-[(tetrahydro-2H-pyran-2-yl)oxy]propoxy]-5-[(tetrahydro-2H-pyran-2-yl)oxy]-2H-cyclopenta[b]furan-2-one A mixture of Intermediate 10a (2.01 g), dihydropyran (2.01 g), and pyridinium toluene-p-sulphonate (0.045 g) in CH$_2$Cl$_2$ (30 ml) was stirred at room temperature for 24 h. Water (30 ml) was added and the aqueous phase extracted with CH$_2$Cl$_2$ (3×30 ml). The combined extracts were washed successively with 8% NaHCO$_3$ (2×40 ml) and brine (2×30 ml) and then dried. Evaporation gave the title compound as an oil (3.18 g).

I.r. (CHBr$_3$) 1770 cm$^{-1}$ $[\alpha]_D^{19.8}+8.6°$ (CH$_3$OH)

The following compounds were prepared in a similar manner:

(b)

[3aR-(3aα,4α,5β,6aα)]-(+)-Hexahydro-4-[3-phenoxy-2-[(tetrahydro-2H-pyran-2-yl)oxy]propoxy]-5-[(tetrahydro-2H-pyran-2-yl)oxy]-2H-cyclopenta[b]furan-2-one, from Intermediate 10b I.r. (CHBr$_3$) 1764 cm$^{-1}$ $[\alpha_D^{9.6}+6.6°$ (CH$_3$OH)

(c)

[3aR-(3aα,4α,5β,6aα)]-(+-(4-[3-(4-Fluorophenoxy)-2-[(tetrahydro-2H-pyran-2-yl)oxy]propoxy]hexahydro-5-[(tetrahydro-2H-pyran-2-yl)oxy]-2H-cyclopenta[b]furan-2-one, from Intermediate 10c.

I.r. (CHBr$_3$) 1765 cm$^{-1}$.

(d)

[3aR-(3aα,4α,5β,6aα)]-(+)-4-[3-(4-Chlorophenoxy)-2-[(tetrahydro-2H-pyran-2-yl)oxy]propoxy]hexahydro-5-(tetrahydro-2H-pyran-2-yl)oxy]-2H-cyclopenta[b]furan-2-one, from Intermediate 10d.

I.r. (CHBr$_3$) 1766 cm$^{-1}$.

(e)

[3aR-(3aα,4α,5β,6aα)]-(+)-4-[3-(3-Chlorophenoxy)-2-[(tetrahydro-2H-pyran-2-yl)oxy]propoxy]hexahydro-5-[(tetrahydro-2H-pyran-2-yl)oxy]-2H-cyclopenta[b]furan-2-one, from Intermediate 10e.

I.r. (CHBr$_3$) 1760 cm$^{-1}$. [α]$_D^{19.6}$+5.6° (CH$_3$OH)

(f)

[3aR-(3aα,4α,5β,6aα)]-(+)-4-[3-(2-Chlorophenoxy)-2-[(tetrahydro-2H-pyran-2-yl)oxy]propoxy]hexahydro-5-[(tetrahydro-2H-pyran-2-yl)oxy]-2H-cyclopenta[β]furan-2-one, from Intermediate 10f.

I.r. (CHBr$_3$) 1760 cm$^{-1}$.

(g)

[3aR-(3aα,4α,5β,6aα)]-(+-Hexahydro-4-[3-(4-methoxyphenoxy)-2-[(tetrahydro-2H-pyran-2-yl)oxy]propoxy]-5-(tetrahydro-2H-pyran-2-yl)oxy]-2H-cyclopenta[b]furan-2-one, from Intermediate 10f.

I.r. (CHBr$_3$) 1760 cm$^{-1}$ (h)

[3aR-(3aα,4α,5β,6aα)-(+)-Hexahydro-4-[3-(3-methylphenoxy)-2-[(tetrahydro-2H-pyran-2-yl)oxy]propoxy]-5-[(tetrahydro-2H-pyran-2-yl)oxy]-2H-cyclopenta[b]furan-2-one, from Intermediate 10h.

I.r. (CHBr$_3$) 1760 cm$^{-1}$ (i)

[3aR-(3aα,4α,5β,6aα)]-+-(Hexahydro-4-[3-[4-(methylthio)phenoxy]-2-[(tetrahydro-2H-pyran-2-yl)oxy]propoxy]-5-[(tetrahydro-2H-pyran-2-yl)oxy]-2H-cyclopenta[b]furan-2-one, from Intermediate 10i I.r. (CHBr$_3$) 1765 cm$^{-1}$. [α]$_D^{19.2}$+7.2° (CH$_3$OH)

(j)

(3aα,4α,5β,6aα)-(±)-Hexahydro-5-[(tetrahydro-2H-pyran-2-yl)oxy]-4-[2-[(tetrahydro-2H-pyran-2-yl)oxy]-3-[3-(trifluoromethyl)phenoxy]propoxy]-2H-cyclopenta[b]furan-2-one, from Intermediate 10j.

I.r. (Neat) 1770 cm$^{-1}$ (k)

[1S-(1α,2β,3α,5α)]-(+)-2-[3-Phenoxy-2-[(tetrahydro-2H-pyran-2-yl)oxy]propoxy]-5-(phenylmethoxy)-3-[(tetrahydro-2H-pyran-2-yl)oxy]cyclopentanepropanal, from Intermediate 25.

I.r. (CHBr$_3$) 1715 cm$^{-1}$ [α]$_D^{20.2}$+24.5° (CH$_3$OH)

(l)

[3aR-(3aα,4α,5β,6aα)-(+)-Hexahydro-4-[2-methyl-2-[(tetrahydro-2H-pyran-2-yl)oxy]-3-phenoxypropoxy]-5-[(tetrahydro-2H-pyran-2-yl)oxy]-2H-cyclopenta[b]furan-2-one, from Intermediate 10k.

I.r. (CHBr$_3$) 1768 cm$^{-1}$ [α]$_D^{23.2}$+2.5° (CH$_3$OH)

Intermediate 12

(a)

[3aR-[3aα,4α(2R*),5β,6aα]]-(+)-Hexahydro-4-[3-phenoxy-2-[(tetrahydro-2H-pyran-2-yl)oxy]propoxy]-5-[(tetrahydro-2H-pyran-2-yl)oxy]-2H-cyclopenta[b]furan-2-ol DIBAL (1M in hexane, 1.09 ml) was added to a cold (−78°), stirred solution of Intermediate 11a (0.4 g) in CH$_2$Cl$_2$ (30 ml). After 1.5 h methanol (25 ml) was added dropwise and after 1 h at room temperature ether (50 ml) was added. After a further 2 h at room temperature the mixture was filtered through hyflo and the filtrate evaporated to give the title compound as an oil (0.37 g).

I.r. (CHBr$_3$) 3580, 3380 cm$^{-1}$

The following compounds were prepared in a similar manner:

(b)

[3aR-(3aα,4α,5β,6aα)-(−)-hexahydro-4-[3-phenoxy-2-[(tetrahydro-2H-pyran-2-yl)-oxy]propoxy]-3-[(tetrahydro-2H-pyran-2-yl)oxy]-2H-cyclopenta[b]furan-2-ol, from Intermediate 11b I.r. (CHBr$_3$) 3580, 3380 cm$^{-1}$ [α]$_D^{20.6}$−13.1° (CH$_3$OH)

(c)

[3aR-(3aα4α,5β,6aα)-(−)-4-[3-(4Fluorophenoxy)-2-[(tetrahydro-2H-pyran-2-yl)oxy]propoxy]hexahydro-5-[(tetrahydro-2H-pyran-2-yl)oxy]-2H-cyclopenta[b]furan-2-ol, from Intermediate 11c.

I.R. (CHBr$_3$) 3580, 3400 cm$^{-1}$. [α]$_D^{22.2}$−16.2° (CH$_3$OH)

(d)

[3aR-(3aα,4α,5β,6aα)]-(−)-4-[3-(4-Chlorophenoxy)-2-[(tetrahydro-2H-pyran-2-yl)oxy]propoxy]hexahydro-5-[(tetrahydro-2H-pyran-2-yl)oxy]-2H-cyclopenta[b]furan-2-ol, from Intermediate 11d.

I.r. (CHBr$_3$) 3580 cm$^{-1}$ (e)

[3aR-(3aα,4α,5β,6aα)]-(−)-4-[3-(3-Chlorophenoxy)-2-[(tetrahydro-2H-pyran-2-yl)oxy]propoxy]hexahydro-5-[(tetrahydro-2H-pyran-2-yl)oxy]-2H-cyclopenta[b]furan-2-ol, from Intermediate 11e.

I.r. (CHBr$_3$) 3580, 3380 cm$^{-1}$. [α]$_D^{22.3}$−12.6° (CH$_3$OH)

(f)

[3aR-(3aα,4α,5β,6aα)-(−)-4-[3-(2-Chlorophenoxy)-2-[(tetrahydro-2H-pyran-2-yl)oxy]propoxy]hexahydro-5-[(tetrahydro-2H-pyran-2-yl)oxy]-2H-cyclopenta[b]furan-2-ol, from Intermediate 11f.

I.r. (CHBr$_3$) 3590, 3560 cm$^{-1}$.

(g)

[3aR-(3aα,4α,5β,6aα)]-(−)-Hexahydro4[3-(4-methoxyphenoxy)-2-[(tetrahydro-2H-pyran-2-yl)oxy]propoxy]-5-[(tetrahydro-2H-pyran-2-yl)oxy]-2H-cyclopenta[b]furan-2-ol, from Intermediate 11g.

I.r. (CHBr$_3$) 3580, 3400 cm$^{-1}$ (h)

[3aR-(3aα,4α,5β,6aα)]-(−)-Hexahydro4[3-(3-methylphenoxy)-2-[(tetrahydro-2H-pyran-2-yl)oxy]propoxy]-5-[(tetrahydro-2H-pyran-2-yl)oxy]-2H-cyclopenta[b]furan-2-ol, from Intermediate 11H.

I.r. (CHBr$_3$) 3580, 3380 cm$^{-1}$ (i)

[3aR-(3aα,4α,5β,6aα)]-(−)-Hexahydro-4-[3-[4-(4-methylthio)phenoxy]-2-[(tetrahydro-2H-pyran-2-yl)oxy]propoxy]-5-[(tetrahydro-2H-pyran-2-yl)oxy]-2H-cyclopenta[b]furan-2-ol, from Intermediate 11i. I.r. (CHBr$_3$) 3580, 3380 cm$^{-1}$. $[\alpha]_D^{21.3}$ −11.9° (CH$_3$OH)

(j)

(3aα,4α,5β,6aα)-(±)-Hexahydro-5-[(tetrahydro-2H-pyran-2-yl)oxy]-4-[2-[(tetrahydro-2H-pyran-2-yl)oxy]-3-[3-(trifluoromethyl)phenoxy]propoxy]-2H-cyclopenta[b]furan-2-ol, from Intermediate 11j.

I.r. (Neat) 3405 cm$^{-1}$ (k) [1R-(Endo, anti)]-(+)-8-(2-Hydroxy-3-phenoxypropoxy)-6-(phenylmethoxy)-2-oxabicyclo[3.2.1]octan-3-ol, from Intermediate 9b.

I.r. (CHBr$_3$) 3400, 1720 cm$^{-1}$ $[\alpha]_D^{18}$ +40.2° (CH$_3$OH)

(l)

[3aR-(3aα,5β,6aα)]-(−)-Hexahydro-4-[2-methyl-2[(tetrahydro-2H-pyran-2-yl)oxy]-3-phenoxypropoxy]-5-[(tetrahydro-2H-pyran-2-yl)oxy]-2H-cyclopenta[b]furan-2-ol, from Intermediate 11l.

I.r. (CHBr$_3$) 3580 cm$^{-1}$ $[\alpha]_D^{20.3}$ −18° (CH$_3$OH)

Intermediate 13

(a) [1S-[1α(Z),2β(2S*),3α,5α]]-(+)-Methyl 7-[5-hydroxy-2-[3-phenoxy-2-[(tetrahydro-2H-pyran-2-yl)oxy]propoxy]-3-[(tetrahydro-2H-pyran-2-yl)oxy]cyclopentyl]-5-heptenoate To a cold (0°) solution of potassium tert-butoxide (1.5 g) in THF (50 ml) under N$_2$ was added (4-carboxybutyl)triphenylphosphonium bromide (3.0 g). After 0.5 h a solution of Intermediate 12a (0.96 g) in THF (30 ml) was added and the mixture stirred at room temperature for 2h. A saturated solution of ammonium chloride (50 ml) was added and the mixture was extracted with ether (3×50 ml). The combined extracts were washed with saturated brine (2×25 ml), dried, esterified with ethereal diazomethane and then evaporated. The residue was purified by chromatography using 2:1 ER-PE (40°-60°) as eluent to give the title compound as an oil (1.0 g).

I.r. (CHBr$_3$) 3520, 1728 cm$^{-1}$ $[\alpha]_D^{23.4}$ +19° (CH$_3$OH)

The following compounds were prepared in a similar manner:

(b) [1S-[1α(Z),2β,3α,5α]]-(+)-Methyl 7-[5-hydroxy-2-[3-phenoxy-2-[(tetrahydro-2H-pyran-2-yl)oxy]propoxy]-3-[(tetrahydro-2H-pyran-2-yl)oxy]cyclopentyl]-5-heptenoate, from Intermediate 12b.

I.r. (CHBr$_3$) 3520, 1728 cm$^{-1}$ $[\alpha]_D^{18.1}$ 18.5° (CH$_3$OH)

(c) [1S-[1α(Z),2β,3α,5α]]-(+)-Mmethyl 7-[2-[3-(4-fluorophenoxy)-2-[(tetrahydro-2H-pyran-2-yl)oxy]propoxy]-5-hydroxy-3-[(tetrahydro-2H-pyran-2-yl)oxy]cyclopentyl]-5-heptenoate, from Intermediate 12c.

I.r. (CHBr$_3$) 3560-3520, 1730 cm$^{-1}$. $[\alpha]_D^{21.3}$ +19.8° (CH$_3$OH)

(d) [1S-[1α(Z),2β,3α,5α]]-(+)-Methyl 7-[2-[3-(4-chlorophenoxy)-2-[(tetrahydro-2H-pyran-2-yl)oxy]propoxy]-5-hydroxy-3-[(tetrahydro-2H-pyran-2-yl)oxy]cyclopentyl]-5-heptenoate, from Intermediate 12d.

I.r. (CHBr$_3$) 3600-3520, 1730 cm$^{-1}$.

(e) [1S-[1α(Z),2β,3α,5α]]-(+)-Methyl 7-[2-[3-(3-chlorophenoxy)-2-[(tetrahydro-2H-pyran-2-yl)oxy]propoxy]-5-hydroxy-3-[(tetrahydro-2H-pyran-2-yl)oxy]cyclopentyl]-5-heptenoate, from Intermediate 12e.

I.r. (CHBr$_3$) 3540, 1730 cm$^{-1}$ $[\alpha]_D^{20.9}$ +20.3° (CH$_3$OH)

(f) [1S-[1α(Z),2β,3α,5α]]-(+)-Methyl 7-[2-[3-(2-chlorophenoxy)-2-[(tetrahydro-2H-pyran-2-yl)oxy]propoxy]-5-hydroxy-3-[(tetrahydro-2H-pyran-2-yl)oxy]cyclopentyl]-5-heptenoate, from Intermediate 12f.

I.r. (CHBr$_3$) 3600-3520, 1730 cm$^{-1}$.

(g) [1S-[1α(Z),2β,3α,5α]]-(+)-Methyl 7-[5-hydroxy-2-[3-(4-methoxyphenoxy)-2-[(tetrahydro-2H-pyran-2-yl)oxy]propoxy]-3-[(tetrahydro-2H-pyran-2-yl)oxy]cyclopentyl]-5-heptenoate, from Intermediate 12 g. I.r. (CHBr$_3$) 3540, 1730 cm$^{-1}$ (h) [1S-[1α(Z),2β, 3α,5α]]-(+)-Methyl 7-[5-hydroxy-2-[3-(3-methylphenoxy)-2-[(tetrahydro-2H-pyran-2-yl)oxy]propoxy]-3-[(tetrahydro-2H-pyran-2-yl)oxy]cyclopentyl-5-heptenoate, from Intermediate 12h. I.r. (CHBr$_3$) 3540, 1720 cm$^{-1}$ $[\alpha]_D^{20}$ +19.1° (CH$_3$OH)

(i) [1S-[1α(Z),2β,3α, 5α]]-(+)-Methyl 7-[5-hydroxy-2-[3[4-(methylthio)phenoxy]-2-[(tetrahydro-2H-pyran-2-yl)oxy]propoxy]-3-[(tetrahydro-2H-pyran-2-yl)oxy]cyclopentyl]-5-heptenoate, from Intermediate 12i. I.r. (CHBr$_3$) 3500, 1723 cm$^{-1}$. $[\alpha]_D^{20.2}$ +21.4° (CH$_3$OH)

(j) [1α(Z),2β,3α,5α]]-(±)-Methyl 7-[5-hydroxy-3-[(tetrahydro-2H-pyran-2-yl)oxy]-2-[2-[(tetrahydro-2H-pyran-2-yl)oxy]-3-[3-(trifluoromethyl)phenoxy]propoxy]cyclopentyl]-5-heptenoate, from Intermediate 12j. I.r. (Neat) 3460, 1738 cm$^{-1}$ (k) [1S-[1α(Z),2β,5α]]-(+)-Methyl 7-[5-hydroxy-2-[3-phenoxy-2-[(tetrahydro-2H-pyran-2-yl)oxy]propoxy]-3-[(tetrahydro-2H-pyran-2-yl)oxy]cyclopentyl]-4-heptenoate, from Intermediate 11k but using (3-carboxypropyl)triphenylphosphonium bromide.

I.r. (CHBr$_3$) 3540, 1730 cm$^{-1}$ (l) [1S-[1α(Z),2β,3α,5α]]-(+)-Methyl 7-[5-hydroxy-2-[2-methyl-3-phenoxy-2-[(tetrahydro-2H-pyran-2-yl)oxy]propoxy]-3-[(tetrahydro-2H-pyran-2-yl)oxy]cyclopentyl]-5-heptenoate, from Intermediate 12l.

I.r. (CHBr$_3$) 3520, 1720 cm$^{-1}$ $[\alpha]_D^{20.1}$ +19.2° (CH$_3$OH)

(m) [1S-(1α,2β,3α)]-(+)-Methyl 7-[5-hydroxy-2-[3-phenoxy-2-[(tetrahydro-2H-pyran-2-yl)oxy]propoxy]-3[(tetrahydro-2H-pyran-2-yl)oxy]cyclopentyl]heptanoate A solution of Intermediate 13b (0.912 g) in ethanol (30 ml) was hydrogenated over pre-reduced 10% palladium oxide on charcoal (0.08 g) at N.T.P. for 16 h. The catalyst and solvent were removed to give the title compound as an oil (0.89 g). I.r. (CHBr₃) 3520, 1725 cm⁻¹. $[\alpha]_D^{18.6}$ +9.4° (CH₃OH)

(n) [1S-[1α(E),2β(2S*),3α]]-(+)-Methyl 7-[5-Hydroxy-2-[3-phenoxy-2-[(tetrahydro-2H-pyran-2-yl)oxy]propoxy]-3-[(tetrahydro-2H-pyran-2-yl)oxy]cyclopentyl]-5-heptenoate A solution of Intermediate 13a (0.2 g), thiophenol (0.55 ml) and azobisisobutyronitrile (0.1 g) in dry benzene (2 ml) was heated at reflux for 24 h. Evaporation and purification of the residue by chromatography using 1:1 ER-PE (40°-60°) increasing to ER as eluent gave the title compound as an oil (0.1 g). T.l.c. ER Rf 0.45.

The following compounds were prepared in a similar manner to intermediate 13a):

(o) [1S-[1α(Z),2β(2S*),3α,5α]]-(+)-Methyl 6-[5-hydroxy-2-[3-phenoxy-2-[(tetrahydro-2H-pyran-2-yl)oxy]propoxy]-3-[(tetrahydro-2H-pyran-2-yl)oxy]cyclopentyl]-4-hexenoate, using (3-carboxypropyl)triphenylphosphonium bromide and Intermeidate 12a.

I.r. (CHBr₃) 3580, 3510, 1725 cm⁻¹. $[\alpha]_D^{23}$ +13.2° (CH₃OH)

(p) [1S-[1α(Z),2β(2S*),3α,5α]]-(+)-Methyl 8-[5-hydroxy-2-[3-phenoxy-2-[(tetrahydro-2H-pyran-2-yl)oxy]propoxy]-3-[(tetrahydro-2H-pyran-2-yl)oxy]cyclopentyl]-6-octenate, using (5-carboxypentyl)triphenylphosphonium bromide and Intermediate 12a.

I.r. (CHBr₃) 3580, 3520, 1725 cm⁻¹. $[\alpha]_D^{23.1}$ +10.6° (CH₃OH)

(q) [1S-[1α(Z),2β(2S*),3α,5α]]-(+)-Methyl 9-[5-hydroxy-2-[3-phenoxy-2-[(tetrahydro-2H-pyran-2-yl)oxy]propoxy]-3-[(tetrahydro-2H-pyran-2-yl)oxy]cyclopentyl]-7-nonenoate, using (6-carboxyhexyl)triphenylphosphonium bromide and Intermediate 12a.

I.r. (CHBr₃) 3580, 3520, 1725 cm⁻¹. $[\alpha]_D^{23.4}$ +12.7° (CH₃OH)

Intermediate 14

(a) [1R-[1α(Z),2β, ((2R*),3α]]-(−)-Methyl 7-[5-oxo-2-[3-phenoxy-2-[(tetrahydro-2H-pyran-2-yl)oxy]propoxy]-3-[(tetrahydro-2H-pyran-2-yl)oxy]cyclopentyl]-5-heptenoate A cold (0°), stirred suspension of Intermediate 13a (0.3 g) and sodium acetate (0.11 g) in CH₂Cl₂ (30 ml) was treated with pyridinium chlorochromate (0.29 g) portionwise during 0.5 h. The mixture was stirred at room temperature for 2 h, diluted with ether (30 ml) and then stirred for a further 0.5 h. Filtration and evaporation gave a residue which was purified by chromatography on acid washed (pH 3.8) silica using 5:3 ER-PE (40°-60°) as eluent to give the title compound as an oil (0.21 g). I.r. (neat) 1740 cm⁻¹ $[\alpha]_D^{23}$ −12.4° (CH₃OH)

The following compounds were prepared in a similar manner:

(b) [1R-[1α(Z),2β, 3α]]-(−)-Methyl 7-[5-oxo-2-[3-phenoxy-2-[(tetrahydro-2H-pyran-2-yl)oxy]propoxy]-3-[(tetrahydro-2H-pyran-2-yl)oxy]cyclopentyl]-5-heptenoate, from Intermediate 13b.

I.r.(CHBr₃) 1740 cm⁻¹ $[\alpha]_D^{19.6}$ −18.6° (CH₃OH)

(c) [1R-[1α(Z),2≢2,3α]]-(−)-Methyl 7-[2-[3-(4-fluorophenoxy)-2-[(tetrahydro-2H-pyran-2-yl)oxy]propoxy]-5-oxo-3-[(tetrahydro-2H-pyran-2-yl)oxy]cyclopentyl]-5-heptenoate, from Intermediate 13c. I.r. (CHBr₃) 1732 cm⁻¹. $[\alpha]_D^{18.3}$ −15.5° (CH₃OH)

(d) [1R-[1α(Z),2β,3α]]-(−)-Methyl 7-[2-[3-(4-chlorophenoxy)-2-[(tetrahydro-2H-pyran-2-yl)oxy]propoxy]-5-oxo-3-[(tetrahydro-2H-pyran-2-yl)oxy]cyclopentyl]-5-heptenoate, from Intermediate 13d. I.r. (CHBr₃) 1730 cm⁻¹.

(e) [1R-[1α(Z),2β,3α]]-(−)-Methyl 7-[2-[3-(3-chlorophenoxy)-2-[(tetrahydro-2H-pyran-2-yl)oxy]propoxy]-5-oxo-3-[(tetrahydro-2H-pyran-2-yl)oxy]cyclopentyl]-5-heptenoate, from Intermediate 13e. I.r. (CHBr₃) 1732 cm⁻¹. $[\alpha]_D^{20.4}$ −12.9° (CH₃OH)

(f) [1R-[1α(Z),2β,3α]]-(−)-Methyl 7-[2-[3-(2-chlorophenoxy)-2-[(tetrahydro-2H-pyran-2-yl)oxy]propoxy]-5-oxo-3-[(tetrahydro-2H-pyran-2-yl)oxy]cyclopentyl]-5-heptenoate, from Intermediate 13f. I.r. (CHBr₃) 1730 cm⁻¹.

(g) [1R-[1α(Z),2β,3α]]-(−)-Methyl 7-[2-[3-(4-methoxyphenoxy)-2-[(tetrahydro-2H-pyran-2-yl)oxy]propoxy]-5-oxo-3-[(tetrahydro-2H-pyran-2-yl)oxy]cyclopentyl-5-heptenoate, from Intermediate 13g.

I.r. (CHBr₃) 1740 cm⁻¹

(h) [1R-[1α(Z),2β,3α]]-(−)-Methyl 7-[2-[3-(3-methylphenoxy)-2-[(tetrahydro-2H-pyran-2-yl)oxy]propoxy]-5-oxo-3-[(tetrahydro-2H-pyran-2-yl)oxy]cyclopentyl-5-heptenoate, from Intermediate 13h.

I.r. (CHBr₃) 1740 cm⁻¹ $[\alpha]_D^{20.5}$ −16° (CH₃OH)

(i) [1R-[1α(Z),2β,3α]]-(±)-Methyl 7-[2-[3-(4-(methylthio)phenoxy)-2-[(tetrahydro-2H-pyran-2-yl)oxy]propoxy]-5-oxo-3-[(tetrahydro-2H-pyran-2-yl)oxy]cyclopentyl]-5-heptenoate A solution of Intermediate 13i (0.1 g) and dicyclohexylcarbodiimide (0.12 g) in dry DMSO (1.5 ml) at ambient temperature was treated with pyridinium trifluoroacetate (0.046 g). After stirring for 4 h the mixture was poured into water (20 ml) and the product extracted with ER (4×30 ml). The combined extracts were dried and evaporated to leave a residue which was purified by chromatography using 5:3 ER-PE as eluent to give the title compound as an oil (0.042 g).

T.l.c. 1:1 EA-PE Rf 0.6.

The following compounds were prepared in a similar manner to Intermediate 14a:

(j) [1α(Z),2β,3α]-(±)-Methyl
7-[5-oxo-3-[(tetrahydro-2H-pyran-2-yl)oxy]-2-[2-[(tetrahydro-2H-pyran-2-yl)oxy]-3-[3-(trifluoromethyl)-phenoxy]propoxy]cyclopentyl]-5-heptenoate, from Intermediate 13j. I.r. (Neat) 3420, 1740 cm$^{-1}$ (k) [1R-[1α(Z),2β,3α]]-(±)-Methyl
7-[2-[3-[4-(methylsulphinyl)
phenoxy]-2-[(tetrahydro-2H-pyran-2-yl)oxy]propoxy]-5-oxo-3-[(tetrahydro-2H-pyran-2-yl)oxy]cyclopentyl]-5-heptenoate from Intermediate 13i. I.r. (CHBr$_3$) 1735 cm$^{-1}$.

(l)
[1R-[1α(Z),2β,(2R*),3α]]-(−)-7-[5-oxo-2-[3-phenoxy-2-[(tetrahydro-2H-pyran-2-yl)oxy]propoxy]-3-[(tetrahydro-2H-pyran-2-yl)oxy]cyclopentyl-5-heptenoic acid, from Intermediate 23.

I.r. (CHBr$_3$) 3500, 1730, 1710 cm$^{-1}$ $[α]_D^{20.6}$ −5° (CH$_3$OH)

(m) [1R-[1α(Z),2β,3α]]-(±)-Methyl
7-[5-oxo-2-[3-phenoxy-2-[(tetrahydro-2H-pyran-2-yl)oxy]propoxy-3-[(tetrahydro-2H-pyran-2-yl)oxy] cyclopentyl]-4-heptenoate, from Intermediate 13k.

I.r. (CHBr$_3$) 1740 cm$^{-1}$ (n) [1R-[1α(Z),2β,3α]]-(−)-Methyl
7-[2-[2-methyl-3-phenoxy-2-[(tetrahydro-2H-pyran-2-yl)oxy]propoxy]-5-oxo-3-[(tetrahydro-2H-pyran-2-yl)oxy]cyclopentyl]-5-heptenoate, from Intermediate 13l.

I.r. (CHBr$_3$) 1740 cm$^{-1}$ $[α]_D^{22}$ −6.8° (CH$_3$OH)

(o) [1R-(1R-(1α,2β,3α)]-(±)-Methyl
7-[5-oxo-2-[3-phenoxy-2-[(tetra
hydro-2H-pyran-2-yl)oxy]propoxy]-3-[(tetrahydro-2H-pyran-2-yl)oxy] cyclopentyl]heptanoate, from Intermediate 13m.

I.r. (CHBr$_3$) 1732 cm$^{-1}$.

(p) [1R-[1α(E),2β(2R*),3α]]-(±)-Methyl
7-[5-oxo-2-[3-phenoxy-2-[(tetrahydro-2H-pyran-2-yl)oxy]propoxy]-3-[(tetrahydro-2H-pyran-2-yl)oxy]cyclopentyl]-5-heptenoate A mixture of N,N'-dicylcohexylcarbodiimide (0.28 g), DMSO (0.23 ml) and Intermediate 13n (0.091 g) in dry CH$_2$Cl$_2$ (2 ml) under nitrogen was treated with pyridinium trifluoroacetate (0.11 g). After stirring for 5 h at 20° water (0.1 ml) and ether (70 ml) were added. The organic phase was washed with copper sulphate solution (20 ml), brine (20 ml) and then dried. Evaporation gave a residue which was purified by chromatography using 2:1 ER-PE (40°-60°) as eluent to give the title compound as an oil (0.073 g). T.l.c. 2:1 ER-PE (40°-60°) Rf 0.28

The following compounds were prepared in a similar manner to Intermediate 14p:

(q)
[1R-[1α(Z),2β(2R*),3α]]-(−)-Methyl-6-[5-oxo-2-[3-phenoxy-2-[(tetrahydro-2H-pyran-2-yl)oxy]propoxy]-3-[(tetrahydro-2H-pyran-2-yl)-oxy]cyclopentyl]-4-hexenoate, from Intermediate 13o.

I.r. (CHBr$_3$) 1740 cm$^{-1}$. $[α]_D^{22.8}$ −23.3° (CH$_3$OH)

(r) [1R-[1α(Z),2β(2R*),3α]]-(−)-Methyl
8-[5-oxo-2-[3-phenoxy-2-[(tetrahydro-2H-pyran-2-yl)oxy]propoxy]-3-[(tetrahydro-2H-pyran-2-yl)oxy]cyclopentyl]-6-octenoate, from Intermedite 13p. I.r. (CHBr$_3$) 1740 cm$^{-1}$. $[α]_D^{22.8}$ −22.3° (CH$_3$OH)

(s) [1R-[1α(Z),2β(2R*),3α]]-(−)-Methyl
9-[5-oxo-2-[3-phenoxy-2-[(tetrahydro-2H-pyran-2-yl)oxy]propoxy]-3-[(tetrahydro-2H-pyran-2-yl)oxy]cyclopentyl]-7-nonenoate, from Intermediate 13q. I.r. (CHBr$_3$) 1740 cm$^{-1}$ $[α]_D^{22.9}$ −23.4° (CH$_3$OH)

(t) [1R-[1α(Z),2β(2R*),3α]]-(−)-1-Methylethyl
7-[5-oxo-2-[3-phenoxy-2-[(tetrahydro-2H-pyran-2-yl)oxy]propoxy]-3-[(tetrahydro-2H-pyran-2-yl)oxy]cyclopentyl]-5-heptenoate, from Intermediate 28. I.r. (CHBr$_3$) 1740, 1720cm$^{-1}$.$[α]_D^{21.4}$ −19.5° (CH$_3$OH)

The following compound was prepared in a similar manner to Intermediate 14a:

(u) [1R-(1α,2β,3α)]-(−)-Methyl
7-[5-oxo-2-[3-phenoxy-2-[(tetrahydro-2H-pyran-2-yl)oxy]propoxy]-3-[(tetrahydro-2H-pyran-2-yl)oxy]cyclopentyl]-4,5-heptadienoate, from Intermediate 32. I.r. (CHBr$_3$) 1735 cm$^{-1}$.

Intermediate 15

(a)
[1R-(Endo,Anti)]-(±)-8-[(2,2-Dimethyl-1,3-dioxolan-4-yl)
methoxy]-6-(phenylmethoxy)-2-oxabicyclo[3.2.1]-octan-3-one Peracetic acid (6.1M, 60 ml) was added dropwise during 15 min to a cold (0°), stirred mixture of Intermediate 7b (50 g) and sodium acetate (29.7 g) in CH$_2$Cl$_2$ (500 ml). After 1 h at 0° the mixture was stirred for 16 h at room temperature and then poured onto 20% sodium sulphite solution (800 ml). The aqueous phase was extracted with CH$_2$Cl$_2$ (3×100 ml) and the combined extracts were washed successively with water (2×75 ml), 8% NaHCO$_3$ (2×75), and then water (3×75 ml). Drying and evaporation gave a viscous gum (50 g) a portion of which (20.2 g) in acetonitrile (200 ml) at 0° was treated with 0.2N NaOH (200 ml). After 1.75 h stirring, brine (100 ml) was added and the mixture extracted with ER (3×100 ml). The dried organic extracts were evaporated to leave a residue which was purified by chromatography using 3:2 EA-PE as eluent to give the title compound as an oil (5.6 g). T.l.c. 2:1 EA-PE Rf 0.2

The following compound was prepared in a similar manner:

(b)
[1R-(Endo,Anti)]-(−)-6-(Phenylmethoxy)-8-(2-propenyloxy)-2-oxabicyclo[3.2.1]octan-3-one, from Intermediate 7c.

I.r. (CHBr$_3$) 1730 cm$^{-1}$ $[α]_D^{19.7}$ −37.5° (CH$_3$OH)

Intermediate 16

(a)
[3aR-(3aα,4α,5β,6aα)]-(+)-4-(2,3-Dihydroxypropoxy)-hexahydro-5-hydroxy-2H-cyclopenta[b]furan-2-one A solution of Intermediate 15a (3.78 g) in ethanol (50 ml) was hydrogenated over pre-reduced 10% palladium on charcoal (0.75 g) at N.T.P. for 2 h and then the solvent and catalyst were removed. A solution of the residue (2.7 g) in cold (0°) THF (15 ml) was treated with 2N HCl (3 ml) and the mixture then stirred at room temperature for 16 h. The solvent was removed in vacuo to give the title compound as an oil (2.71 g). I.r. (CHBr$_3$) 3580, 1760 cm$^{-1}$ [α]$_D^{21}$ +5.7° (CH$_3$OH)

(b)
[4aR-(4aα,5α,6β,7aα)]-(±)-Octahydro-5-[3-phenoxy-2-[(tetrahydro-2H-pyran-2-yl)oxy]propoxy]-6-[(tetrahydro-2H-pyran-2-yl)oxy]cyclopenta [b] pyran-2-ol A solution of Intermediate 11k (0.16 g) in EA (10 ml) was hydrogenated over pre-reduced 10% palladium on charcoal (0.016 g) at N.T.P. for 24 h. The catalyst and solvent were removed and the residual oil (0.16 g) purified by chromatography using 7:1 ER-PE (40°-60°) as eluent to give the title compound as an oil (0.086 g). I.r. (CHBr$_3$) 3570 cm$^{-1}$

Intermediate 17

[3aR-(3aα,4α,5β,6aα)]-(+)-Hexahydro-5-hydroxy-4-(oxiranylmethoxy)-2Hcyclopenta[b]furan-2-one A solution of Intermediate 16 (0.5 g) and triphenylphosphine (0.85 g) in DMSO (0.5 ml) and 1,4-dioxan (5 ml) at 70° was treated with a solution of diethyl azodicarboxylate (0.7 ml) in dioxan (2 ml) over 5 min and the mixture heated for 5 h. The solvent was removed in vacuo and the residue purified by chromatography using 2:1 EA-PE then EA as eluent to give the title compound as a solid (0.33 g). A portion was crystallised from methyl acetate-PE m.p. 100°-102°. [α]$_D^{21.1}$ +8° (CH$_3$OH)

Intermediate 18

(±)-1-(Phenylmethoxy)-3-[3-(trifluoromethyl)phenoxy]propan-2-ol

Sodium hydride (80% dispersion in oil, 0.045 g) was added to a mixture of benzyl alcohol (4 ml) and THF (3 ml) and warmed gently until effervescence ceased. To the cooled solution was added 1,2-epoxy-3-[3-(trifluoromethyl)phenoxy]propane (2.12 g). After stirring for 3 h the mixture was poured into ER (50 ml) and washed with brine. The dried extracts were evporated and the residue distilled (b.p. 140°-144°/0.03 mm) to yield the title compound as an oil (2.25 g). I.r. (Neat) 3420 cm$^{-1}$

Intermediate 19

(±)-2-[1-[(Phenylmethoxy)methyl]-2-[3-(trifluoromethyl)phenoxy]ethoxy]tetrahydro-2H-pyran A solution of Intermediate 18 (103 g), dihydropyran (100 g) and toluene-p-sulphonic acid (0.1 g) in ER (350 ml) was allowed to stand at room temperature for 16 h. The solution was extracted with 8% NaHCO$_3$ solution and the aqueous layer then extracted with ER (2×100 ml). The combined organic extracts were dried and evaporated to yield the title compound as an oil (115 g). I.r. (Neat) 1330 cm$^{-1}$

Intermediate 20

(±)-2-[(Tetrahydro-2H-pyran-2-yl)oxy]-3-[3-(trifluoromethyl)phenoxy]propan-1-ol

A solution of Intermediate 19 (66.0 g) in ethanol (500 ml) was hydrogenated over pre-reduced 10% palladium oxide on charcoal (12 g) at 40 p.s.i. The catalyst and solvent were removed to afford the title compound as an oil (52.0 g). I.r. (Neat) 3420 cm$^{-1}$

Intermediate 21

(Endo)-(±)-3-(Phenylmethoxy)tricyclo[3.2.0.0$^{2,7}$]heptan-6-one

Prepared as described in Belgian Patent Specification No. 848992.

Intermediate 22

(Endo,Anti)-(±)-7-[2-Hydroxy-3-[3-(trifluoromethyl)phenoxy]propoxy]-5-(phenylmethoxy)bicyclo[2.2.1]heptan-2-one Sodium hydride (80% dispersion in oil; 3 g) was added to a stirred solution of Intermediate 20 (32 g) in THF (30 ml) at 0°, under N$_2$. A solution of Intermediate 21 (26.7 g) in THF (30 ml) was added rapidly and after 3 h at room temperature the reaction mixture was poured into saturated ammonium chloride solution. The aqueous mixture was extracted with ER (3×150 ml), the combined extracts washed with water (2×100 ml), dried and then evaporated to give a viscous oil (63 g). The crude product in acetone (400 ml) and 2N HCl (90 ml) was stirred at room temperature for 16 H, neutralised with 8% NaHCO$_3$ and then extracted with ether (3×150 ml). Drying and evaporation gave a residue which was purified by chromatography using 9:1 ER-PE as eluent to give the title compound as an oil (20.25 g). I.r. (Neat) 3450, 1750 cm$^{-1}$

Intermediate 23

[1S-[1α(Z),2β(2S*),3α,6α]]-(±)-7-[5-Hydroxy-2-[3-phenoxy-2-[(tetrahydro-2H pyran-2-yl)oxy]propoxy]-3-[(tetrahydro-2H-pyran-2-yl)oxy]cyclopentyl]-5-heptenoic acid The procedure for Intermediate 13a was repeated using Intermediate 12a (0.46 g). The ER extracts, prior to esterification were extracted with 8% NaHCO$_3$ (2×15 ml) and the aqueous extracts treated with a saturated ammonium chloride solution (30 ml). The mixture was extracted with ER (3×50 ml) and the combined extracts washed with brine (15 ml), dried and evaporated to give the title compound as a gum (0.4 g).

I.r. (CHBr$_3$) 3480, 1740, 1709 cm$^{-1}$

Intermediate 24

[1R-(Endo,Anti)-(−)-8-(Oxiranylmethoxy)-6-(phenylmethoxy)-2-oxabicyclo[3.2.1]-octan-3-one To a stirred solution of Intermediate 15b (30.0 g) in 12:1 dioxan-water (200 ml) was added iodine (2.64 g) and silver I oxide (2.4 g). After stirring for 2 h at room temperature, in the dark, further quantities of iodine (1.32 g) and silver I oxide (1.2 g) were added. After a further 2 h the mixture was filtered, the dioxan removed in vacuo and the aqueous residue extracted with ER (3×50 ml). The combined organic extracts were washed successively with brine (3×30 ml), 20% sodium sulphite solution (3×30 ml) and brine (20 ml). The dried extracts were evaporated to yield a solid (4.15 g) a portion of which (2.0 g) in acetonitrile (25 ml) at 0° was treated with 0.2N NaOH (25 ml). After 15 min stirring at room temperature bring (75 ml) was added and the mixture extracted with ER (4×60 ml). The dried extracts were evaporated to yield the title compound as an oil (1.24 g).

I.r. (CHBr$_3$) 1732 cm$^{-1}$ [α]$_D^{20.5}$ −41.3° (CH$_3$OH)

Intermediate 25

[1S-(1α,2β,3α,5α)]-(+)-3-Hydroxy-2-(2-hydroxy-3-phenoxypropoxy)-5-(phenylmethoxy)cyclopentane-propanal To a cold (0°) solution of potassium tert-butoxide (2.91 g) in THF (40 ml), under N$_2$, was added (methoxymethyl)triphenylphosphonium chloride (8.83 g). After 5 min a solution of Intermediate 12k (2.5 g) in THF (25 ml) was added and the mixture stirred at 0° for 2 h. A saturated solution of ammonium chloride (50 ml) was added and the mixture was extracted with ether (4×50 ml). The combined extracts were washed with brine (2×30 ml), dried and evaporated to yield an oil (8.9 g). The crude product was stirred in 1:1 0.25N sulphuric acid-acetone (80 ml) for 24 h at ambient temperature. The organic solvent was then removed in vacuo and the aqueous residue extracted with EA (4×70 ml). The combined organic phases were washed with saturated brine (2×30 ml), dried and evaporated. The residue was purified by chromatography using ER as eluent to give the title compound as an oil (1.9 g).

I.r. (CHBr$_3$) 3600–3200, 1718 cm$^{-1}$ [α]$_D^{21}$+33° (CH$_3$OH)

Intermediate 26

[1R-(Endo,anti)]-(−)-8-(2-Oxo-3-phenoxypropoxy)-6-(phenylmethoxy)-2-oxabicyclo[3.2.1]-octan-3-one A solution of pyridine-sulphur trioxide complex (2.58 g) in dry dimethylsulphoxide (6 ml) was added to a solution of Intermediate 9b (1.41 g) and triethylamine (3.1 ml) in dry CH$_2$Cl$_2$ (6 ml) under N$_2$ and the mixture stirred for 3h. Saturated ammonium chloride solution (5 ml) and water (5 ml) were added and the mixture extracted with EA (3×30 ml). The combined organic phases were washed with water and brine, dried, and evaporated in vacuo. The residue was purified by chromatography using 3:1 CHCl$_3$-EA as eluent to give the title compound as an oil (1.21 g). I.r. (CHBr$_3$) 1733 cm$^{-1}$ [α]$_D^{21}$−20° (CHCl$_3$)

Intermediate 27

[1R-(Endo,anti)]-(−)-8-(2-Hydroxy-2-methyl-3-phenoxypropoxy)-6-(phenylmethoxy)-2-oxabicyclo[3.2.1]-octan-3-one A solution of 2.9M methyl magnesium chloride in THF (1.0 ml) was added to a solution of Intermediate 26 (1.1 g) in THF (9 ml), under N$_2$, at 0° and the mixture stirred for 2 h. Further aliquots of methyl magnesium chloride solution (0.5 ml) were added after 1 h and 1.5 h. After a further 1 h saturated ammonium chloride solution (2 ml) and water (8 ml) were added and the mixture extracted with EA (6×15 ml). The dried organic phases were evaporated and the residue purified by chromatography using 1:1 PE-EA as eluent to give the title compound as an oil (0.96 g). I.r. (CHBr$_3$) 3560, 1735 cm$^{-1}$ [α]$_D^{18.9}$−28° (CH$_3$OH)

Intermediate 28

[1S-[1α(Z),2β(2S*),3α,5α]]-(+)-1-Methylethyl 7-[5-hydroxy-2-[3-phenoxy-2-[(tetrahydro-2H-pyran-2-yl)oxy]propoxy]-3-[(tetrahydro-2H-pyran-2-yl)oxy]cyclopentyl]-5-heptenoate A solution of Intermediate 23 (0.5 g) in DMSO (5 ml) was treated with diisopropylamine (0.5 ml) and 2-bromopropane (0.75 ml) and the mixture stirred at room temperature for 5 days. The mixture was poured into saturated ammonium chloride solution (100 ml) and then extracted with EA (2×75 ml). The dried organic phases were evaporated and the residue purified by chromatography using 5:3 ER-PE (40°–60°) as eluent to give the title compound as an oil (0.42 g).

I.r. (CHBr$_3$) 3530, 1720 cm$^{-1}$. [α]$_D^{21.1}$+17.3° (CH$_3$OH)

Intermediate 29

[1S(1α,2β,3α,5α)]-(±)-Methyl 6-hydroxy-7-[5-hydroxy-2-[3-phenoxy-2-[(tetrahydro-2H-pyran-2-yl)oxy]propoxy]-3-[(tetrahydro-2H-pyran-2-yl)oxy]cyclopentyl]-4-heptynoate n-Butyl lithium (1.6M in hexane, 17.4 ml) was added to a solution of diisopropylamine (3.9 ml) and hexamethylphosphoramide (5.0 ml) in ER (40 ml) at 0° under nitrogen. The solution was cooled to −78° and a solution of 4-pentynoic acid (1.37 g) in ER (10 ml) and THF (15 ml) added. The mixture was then allowed to warm to room temperature, and after 1h, a solution of Intermediate 12b (0.9 g) in ER (25 ml) was added. After 18h, a solution of oxalic acid dihydrate (4.0 g) in water (70 ml) was added and the mixture extracted with EA (3×100 ml). The dried organic extracts were esterified with ethereal diazomethane and then evaporated. The residue was purified by chromatography using 9:1 increasing to 4:1 ER-EA as eluent to give the title compound as an oil (0.83 g). I.r. (CHBr$_3$) 3580, 3500, 1728 cm$^{-1}$.

Intermediate 30

[1R-(1α,2β,3α,5α)]-(±)-Methyl 6-acetyloxy-[5-acetyloxy-2-[3-phenoxy-2-[tetrahydro-2H-pyran-2-yl)oxy]propoxy]-3-[(tetrahydro-2H-pyran-2-yl)oxy]cyclopentyl]-4-heptynoate Triethylamine (2.3 ml), acetic anhydride (1.9 ml) and 4-dimethyl aminopyridine (20 mg) were added to a stirred solution of Intermediate 29 (0.8 g) in CH$_2$Cl$_2$ (16 ml). After 2 h, chromatography using 4:1 ER-PE (40°–60°) as eluent gave the title compound as an oil (0.87 g).

I.r. (CHBr$_3$) 1728 cm$^{-1}$.

Intermediate 31

[1R-(1α,2β,3α,5α)]-(±)-Methyl 7-[5-acetyloxy-2-[3-phenoxy-2-[tetrahydro-2H-pyran-2-yl)oxy]propoxy]-3-[(tetrahydro-2H-pyran-2-yl)oxy]cyclopentyl]-4-5-heptadienoate Methyl lithium (1.5M in ER, 13.3 ml) was added to a stirred suspension of cuprous iodide (1.9 g) in ER (40 ml) at −10° under nitrogen. When the addition was complete, a clear solution was obtained which was then cooled to −78° and a solution of the Intermediate 30 (0.85 g) in ER (25 ml) at −78° was added. After 1.5 h, saturated ammonium chloride solution (60 ml) was added and the mixture stirred at room temperature for 1 h. The organic phase was washed with saturated brine (60 ml) and the aqueous phase extracted with ER (80 ml). The dried organic extracts were evaporated and the residue purified by chromatography using 3:2 increasing to 4:1 ER-PE (40°–60°) as eluent to give the title compound as an oil (0.93 g). I.r. (CHBr$_3$) 1960, 1728 cm$^{-1}$.

Intermediate 32

[1S-(1α,2β,3α,5α)]-(−)-Methyl 7-[5-hydroxy-2-[3-phenoxy-2-[tetrahydro-2H-pyran-2-yl)oxy]propoxy]-3-[(tetrahydro-2H-pyran-2-yl)oxy]cyclopentyl]-4,5-heptadienoate Potassium carbonate (1.0 g) was added to a stirred solution of Intermediate 31 (0.56 g) in methanol (15 ml). After 16 h, the mixture was partitioned between ER (50 ml) and 1N hydrochloric acid (30 ml). The aqueous phase was extracted with ER (50 ml) and the organic phases washed with 8% sodium bicarbonate solution (30 ml) and saturated brine (30 ml). The combined aqueous layers were extracted with EA (70 ml) and the dried organic layers were esterified with ethereal diazomethane. Evaporation gave the title compound as an oil (0.52 g).

I.r. (CHBr$_3$) 3580, 3520, 1958, 1725 cm$^{-1}$.

EXAMPLE 1

[1R-[1α(Z),2β,(R*),3α]]-(−)-Methyl 7-[3-hydroxy-2-(2-hydroxy-3-phenoxypropoxy)-5-oxocyclopentyl]-5-heptenoate A solution of Intermediate 14a (0.27 g) in 20:10:3 acetic acid-water-THF (5 ml) was heated at 45° for 3 h. The solvent was removed in vacuo and the residue purified by chromatography on acid-washed (pH 3.8) silica using 3:2 ER-PE (40°-60°) then ER as eluent to give the title compound as an oil (0.11 g).

I.r. (CHBr$_3$) 3590, 3460, 1738 cm$^{-1}$ [α]$_D^{20.5}$ −22° (CH$_3$OH). Analysis Found: C, 65.13; H, 7.72. C$_{22}$H$_{30}$O$_7$ requires C, 65.01; H, 7.44%.

EXAMPLE 2

[1R-[1α(Z),2β,3α]]-(−)-Methyl 7-[3-hydroxy-2-(2-hydroxy-3-phenoxypropoxy)-5-oxocyclopentyl]-5-heptenoate A solution of Intermediate 14b (0.41 g) in 20:10:3 acetic acid-water-THF (5 ml) was heated at 45° for 4 h. The solvent was removed in vacuo and the residue purified by chromatography on acid-washed (pH 3.8) silica using ER as eluent to give the title compound as an oil (0.13 g).

I.r. (CHBr$_3$) 3580, 3460, 1738 cm$^{-1}$. [α]$_D^{18.6}$ −19° (CH$_3$OH). Analysis Found: C, 64.91; H, 7.62. C$_{22}$H$_{30}$O$_7$ requires C, 65.01; H, 7.44%.

EXAMPLE 3

[1R-[1α(Z),2β,3α]]-(−)-Methyl 7-[2-[3-(4-fluorophenoxy)-2-hydroxypropoxy]-3-hydroxy-5-oxocyclopentyl]-5-heptenoate A solution of Intermediate 14c (0.3 g) in 20:10:3 acetic acid-water-THF (3 ml) was heated at 45° for 3 h. The solvent was removed in vacuo and the residue purified by chromatography on acid-washed (pH 3.8) silica using 100:1 ER-methanol as eluent to give the title compound as an oil (0.145 g).

I.r. (CHBr$_3$) 3580, 3460, 1735 cm$^{-1}$. [α]$_D^{21}$ −20.1° (CH$_3$OH). Analysis Found: C, 61.83%, H, 6.89. C$_{22}$H$_{29}$FO$_7$ requires C, 62.25; H, 6.89%

EXAMPLE 4

(a) [1R-[1α(Z),2β,3α]]-(−)-Methyl 7-[2-[3-(4-chlorophenoxy)-2-hydroxypropoxy]-3-hydroxy-5-oxocyclopentyl]-5-heptenoate A solution of Intermediate 14d (0.243 g) in 20:10:3 acetic acid-water-THF (1.5 ml) was heated at 47° for 4.5 h. The solvent was removed in vacuo and the residue purified by chromatography on acid-washed (pH 3.8) silica using 49:1 ER-methanol as eluent to give the title compound as an oil (0.124 g).

Analysis Found: C, 59.89; H, 6.62. C$_{22}$H$_{29}$ClO$_7$ requires C, 59.93; H, 6.63%. [α]$_D^{20.3}$ −12.7° (CH$_3$OH) I.r. (CHBr$_3$) 3580, 3460, 1735 cm$^{-1}$.

The following compounds were prepared in a similar manner:

(b) [1R-[1α(Z),2β,3α]]-(−)-Methyl 7-[2-[3-(3-chlorophenoxy)-2-hydroxypropoxy]-3-hydroxy-5-oxocyclopentyl]-5-heptenoate (0.263 g) from Intermediate 14e (0.46 g) purified using 50:1 ER-methanol as eluent.

Analysis Found: C, 59.93; H, 6.66. C$_{22}$H$_{29}$ClO$_7$ requires C, 59.93; H, 6.63%.

[α]$_D^{20.3}$ −11.3° (CH$_3$OH) I.r. (CHBr$_3$) 3590, 3480, 1740 cm$^{-1}$.

(c) [1R-[1α(Z),2β,3α]]-(−)-Methyl 7-[2-[3-(2-chlorophenoxy)-2-hydroxypropoxy]-3-hydroxy-5-oxocyclopentyl]-5-heptenoate (0.126 g) from Intermediate 14f (0.267 g)

Analysis Found: C, 59.86; H, 6.64. C$_{22}$H$_{29}$ClO$_7$ requires C, 59.93; H, 6.63%.

[α]$_D^{21.3}$ −12.3° (CH$_3$OH) I.r. (CHBr$_3$) 3580, 3460, 1735 cm$^{-1}$.

(d) [1R-[1α(Z),2β,3α]]-(−)-Methyl 7-[3-hydroxy-2-[2-hydroxy-3-(4-methoxyphenoxy)propoxy]-5-oxocyclopentyl]-5-heptenoate (0.106a) from Intermediate 14g (0.2 g) purified using ER as eluent.

Analysis Found: C, 63.06; H, 7.53. C$_{23}$H$_{32}$O$_8$ requires C, 63.29; H, 7.3%.

[α]$_D^{20.7}$ −19.4° (CH$_3$OH) I.r. (CHBr$_3$) 3580, 3400, 1740 cm$^{-1}$.

(e) [1R-[1α(Z),2β,3α]]-(−)-Methyl 7-[3-hydroxy-2-[2-hydroxy-3-(3-methylphenoxy)propoxy]-5-oxocyclopentyl]-5-heptenoate (0.135 g) from Intermediate 14h (0.26 g) purified using ER as eluent.

Analysis Found: C, 65.77; H, 7.51. C$_{23}$H$_{32}$O$_7$ C, 65.69; H, 7.69%.

[α]$_D^{21.5}$ −14.8° (CH$_3$OH) I.r. (CHBr$_3$) 3570, 3450, 1735 cm$^{-1}$.

(f) [1R-[1α(Z),2β,3α]]-(−)-Methyl 7-[3-hydroxy-2-[2-hydroxy-3-(4-methylthio)phenoxy)propoxy]-5-oxocyclopentyl]-5-heptenoate (0.065 g) from Intermediate 14i (0.16 g) purified using ER as eluent.

Analysis Found: C, 60.74; H, 7.05. C$_{23}$H$_{32}$O$_7$S requires C, 61.04; H, 7.13%.

[α]$_D^{18.7}$ −17.1° (CH$_3$OH) I.r. (CHBr$_3$) 3590, 3480, 1740 cm$^{-1}$.

(g) [1R-[1α(Z),2β,3α]]-(−)-Methyl 7-[3-hydroxy-2-[2-hydroxy-3-[4-(methylsulphinyl)-phenoxy]propoxy-5-oxocyclopentyl]-5-heptenoate (0.105 g) from Intermediate 14k (0.215 g) purified using 10:1 ER-methanol as eluent.

Analysis Found: C, 58.57; H, 6.88. $C_{33}H_{32}O_8S$ requires C, 58.96; H, 6.88%.

$[\alpha]_D^{20.5} -13.2°$ (CH$_3$OH) I.r. (CHBr$_3$) 3580, 1740 cm$^{-1}$.

EXAMPLE 5

[1α(Z),2β,3α]-(±)-Methyl 7-[3-hydroxy-2-[2-hydroxy-3-[3-(trifluoromethyl)-phenoxy]propoxy]-5-oxocyclopentyl]-5-heptenoate A solution of Intermediate 14j (0.45 g) in acetone (10 ml) and 0.1N oxalic acid (7 ml) was heated at 50° for 7 h. The reaction mixture was poured into brine (50 ml), extracted with CH$_2$Cl$_2$ (3×50 ml) and dried. Evaporation of the solvent gave a residue which was purified by chromatography using ER as eluent. The title compound was obtained as an oil (0.23 g). I.r. (Neat) 3440, 1740 cm$^{-1}$.

Analysis Found: C, 57.8; H, 6.3. $C_{23}H_{29}F_3O_7$ requires C, 58.2; H, 6.1%.

EXAMPLE 6

[1R-[1α(Z),2β,(R*),3α]]-(−)-7-[3-hydroxy-2-(2-hydroxy-3-phenoxypropoxy)-5-oxocyclopentyl]-5-heptenoate acid A solution of Intermediate 14l (0.21 g) in 20:10:3 acetic acid-water-THF (2 ml) was heated at 45° for 3 h. The solvent was removed in vacuo and the residue purified by chromatography on acid-washed (pH 3.8) silica using 25:25:2 ER-PE-methanol as eluent to give the title compound as an oil (0.04 g).

T.l.c. 19:1 ER-Methanol Rf 0.45 I.r. (CHBr$_3$) 1740, 1700 cm$^{-1}$.

EXAMPLE 7

[1R-[1α(Z),2β,3α]]-(−)-Methyl 7-[3-hydroxy-2-(2-hydroxy-3-phenoxypropoxy)-5-oxocyclopentyl]-4-heptenoate A solution of Intermediate 14m (0.203 g) in 20:10:3 acetic acid-water-THF (1 ml) was heated at 45° for 4 h. The solvent was removed in vacuo and the residue purified by chromatography on acid-washed (pH 3.8) silica using 3:1 EA-PE as eluent to give the title compound as an oil (0.019 g).

I.r. (CHBr$_3$) 3580, 3450, 1738 cm$^{-1}$. Analysis Found: C, 64.61; H, 7.52. $C_{22}H_{30}O_7$ requires C, 65.01; H, 7.44%.

EXAMPLE 8

(a) [1R-[1α(Z),2β,3α]]-(−)-Methyl 7-[3-hydroxy-2-(2-hydroxy-2-methyl-3-phenoxypropoxy)-5-oxocyclopentyl]-5-heptenoate, Isomer I.

A solution of Intermediate 14n (0.443 g) in 20:10:3 acetic acid-water-THF (2 ml) was heated at 45° for 4 h. The solvent was removed in vacuo and the residue purified by chromatography on acid-washed (pH 3.8) silica using 99:1 ER-methanol as eluent to give the title compound as an oil (0.121 g), ISOMER 1.

I.r. (CHBr$_3$) 3580, 3560, 3500, 1735 cm$^{-1}$. T.l.c. 99:1 ER-Methanol Rf 0.25 $[\alpha]_D^{20.4} -8.3°$ (CH$_3$OH)

Further elution gave:

(b) [1R-[1α(Z),2β,3α]]-(−)-Methyl 7-[3-hydroxy-2-(2-hydroxy-2-methyl-3-phenoxypropoxy)-5-oxocyclopentyl]-5-heptenoate, Isomer 2, as an oil (0.125 g)

I.r. (CHBr$_3$) 3580, 3500, 1740 cm$^{-1}$. Analysis Found: C, 65.37; H, 7.76. $C_{23}H_{32}O_7$ requires C, 65.70; H, 7.67%. $[\alpha]_D^{20.4} -0.51°$ (CH$_3$OH) T.l.c. 99:1 ER-Methanol Rf 0.21.

EXAMPLE 9

[1R-(1α,2β,3α)]-(−)-Methyl 7-[3-hydroxy-2-(2-hydroxy-3-phenoxypropoxy)-5-oxocyclopentyl]heptanoate A solution of Intermediate 14o (0.265 g) in 20:10:3 acetic acid-water-THF (1 ml) was heated at 45° for 4.5 h. The solvent was removed in vacuo and the residue purified by chromatography on acid-washed (pH 3.8) silica using 49:1 ER-methanol as eluent to give the title compound as an oil (0.124 g).

Analysis Found: C, 64.44; H, 7.64. $C_{22}H_{32}O_7$ requires C, 64.69; H, 7.90%. $[\alpha]_D^{21} -11.6°$ (CH$_3$OH) I.r. (CHBr$_3$) 3580, 3420, 1735 cm$^{-1}$.

EXAMPLE 10

(a) [1R-[1α(E),2β(R*),3α]]-(−)-Methyl 7-[3-hydroxy-2-(2-hydroxy-3-phenoxypropoxy)-5-oxocyclopentyl]-5-heptenoate A solution of Intermediate 14p (0.066 g) in 20:10:3 acetic acid-water-THF (3.5 ml) was heated at 40° for 5 h. The solvent was removed in vacuo and the residue purified by chromatography on acid-washed (pH 3.8) silica using ER as eluent to give the title compound as an oil (0.037 g). I.r. (CHBr$_3$) 3600, 3450, 1745 cm$^{-1}$.

Analysis Found: C, 64.83; H, 7.69. $C_{22}H_{30}O_7$ requires C, 65.01; H, 7.69%.

The following compounds were prepared in a similar manner:

(b) [1R-[1α(Z),2β(R*),3α]]-(−)-Methyl 6-[3-hydroxy-2-(2-hydroxy-3-phenoxypropoxy)-5-oxocyclopentyl]-4-hexenoate (0.151 g) from Intermediate 14q (0.305 g) purified using 49:1 ER-methanol as eluent.

I.r. (CHBr$_3$) 3585, 3460, 1740 cm$^{-1}$. $[\alpha]_D^{22} -23.0°$ (CH$_3$OH)

(c) [1R-[1α(Z),2β(R*),3α]]-(−)-Methyl 8-[3-hydroxy-2-(2-hydroxy-3-phenoxypropoxy)-5-oxocyclopentyl]-6-octenoate (0.177 g) from Intermediate 14r (0.347 g).

$[\alpha]_D^{22.5} -22.0°$ (CH$_3$OH)

(d) [1R-[1α(Z),2β(R*),3α]]-(−)-Methyl 9-[3-hydroxy-2-(2-hydroxy-3-phenoxypropoxy)-5-oxocyclopentyl]-7-nonenoate (0.183 g) from Intermediate 14s (0.345 g).

$[\alpha]_D^{23.6} -25.2°$ (CH$_3$OH). I.r.

EXAMPLE 11

[1R-[1α(Z),2β(R*),3α]]-(−)-1-Methylethyl 7-[3-hydroxy-2-(2-hydroxy-3-phenoxypropoxy)-5-oxocyclopentyl]-5-heptenoate A solution of Intermediate 14t (0.29 g) in 20:10:3 acetic acid-water-THF (3 ml) was heated at 40° for 4 h. The solvent was removed in vacuo and the residue purified by chromatography on acid-washed (pH 3.8) silica using 75:1 ER-methanol as eluent to give the title compound as an oil (0.155 g).

Analysis Found: C, 66.37; H, 7.89. $C_{24}H_{34}O_7$ requires C, 66.34; H, 7.89%. $[\alpha]_D^{19.7} -22.1°$ ($CH_3OH$) I.r. ($CHBr_3$) 3590, 3470, 1742, 1720 cm$^{-1}$.

EXAMPLE 12

[1R-(1α,2β,3α)]-(−)-Methyl 7-[3-hydroxy-2-(2-hydroxy-3-phenoxy propoxy)-5-oxocyclopentyl]-4,5-heptadienoate A solution of Intermediate 14u (0.39 g) in 20:10:3 acetic acid-water-THF (10 ml) was heated at 45° for 2 h. The solvent was removed in vacuo and the residue purified by chromatography on acid-washed (pH 3.8) silica using 3:1 increasing to 3:2 ER-EA as eluent to give the title compound as an oil (0.223 g).

I.r. ($CHBr_3$) 3580, 3460, 1960, 1735 cm$^{-1}$. Analysis Found: C, 65.21; H, 7.18. $C_{22}H_{28}O_7$ requires C, 65.33; H, 6.98%.

I claim:

1. Compounds of the general formula (I)

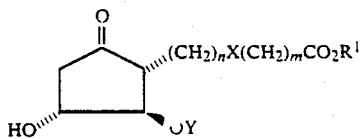

(1)

wherein n is 1 or 2;

m is 2-5 and X is cis or trans —CH=CH— or $CH_2$—$CH_2$—; or m is 1-4 and X is —CH=C=CH—;

$R^1$ is a hydrogen atom, $C_{1-6}$ alkyl or $C_{7-10}$ phenalkyl; and

Y is

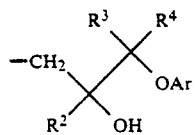

where $R^2$, $R^3$ and $R^4$ are each a hydrogen atom or methyl and at least one is a hydrogen atom, and Ar is a phenyl group (optionally substituted by one or two $C_{1-4}$ alkyl, $C_{1-4}$ alkoxy, $C_{1-4}$ alkylthio, $C_{1-4}$ alkylsulphinyl, $C_{1-4}$ alkylsulphonyl, halogen or trifluoromethyl groups);

and the physiologically acceptable salts and solvates thereof.

2. Compounds as claimed in claim 1 in which X is —CH=CH— or —$CH_2CH_2$— and n is 1 and m is 3 or n is 2 and m is 2 or 4; X is —CH=C=CH—, n is 1 and m is 2; or X is —CH=C=CH—, n is 2 and m is 1 or 3.

3. Compounds as claimed in claim 1 in which $R^1$ is a hydrogen atom or $C_{1-3}$ alkyl.

4. Compounds as claimed in claim 1 in which $R^3$ and $R^4$ are hydrogen atoms.

5. Compounds as claimed in claim 1 in which Ar is phenyl or phenyl substituted by fluoro or chloro.

6. Compounds as claimed in claim 2 in which:
$R^1$ is a hydrogen atom or $C_{1-3}$ alkyl;
$R^2$ is a hydrogen atom or methyl,
$R^3$ and $R^4$ are hydrogen atoms, and
Ar is phenyl, chlorophenyl or fluorophenyl.

7. Compounds as claimed in claim 1 in which the carbon atom carrying the —$(CH_2)_n$ X $(CH_2)_m$ $COOR^1$ group is in the R-configuration.

8. Compounds as claimed in claim 1, said compounds being:
[1R-[1α(Z),2β,(R*),3α]]-(−)-Methyl 7-[3-hydroxy-2-(2-hydroxy-3-phenoxypropoxy)-5-oxocyclopentyl]-5-heptenoate, or
[1R-[1α(Z),2β,(R*),3α]]-7-[3-hydroxy-2-(2-hydroxy-3-phenoxypropoxy)-5-oxocyclopentyl]-5-heptenoic acid and its physiologically acceptable salts.

9. A pharmaceutical composition comprising a compound as claimed in claim 1 together with one or more pharmaceutical carriers.

10. A process for the preparation of a compound as claimed in claim 1 which comprises:

(a) deprotecting a corresponding compound in which the ring hydroxy group and the hydroxy group in Y are protected;

(b) in the preparation of a compound in which $R^1$ is $C_{1-6}$ alkyl or $C_{7-10}$ phenalkyl, esterifying the corresponding compound in which $R^1$ is a hydrogen atom;

(c) in the preparation of a compound in which X is —$CH_2CH_2$—, reducing the corresponding compound in which X is —CH=CH—, or an acetylene group;

(d) in the preparation of a compound in which X is —CH=CH—, selectively reducing the corresponding compound in which X is an acetylene group;

(e) in the preparation of a compound in which $R^1$ is a hydrogen atom, hydrolysing a corresponding ester; or (f) treating an acid of formula (1) with a base to form a salt.

* * * * *